(12) United States Patent
Yuan et al.

(10) Patent No.: US 10,865,225 B2
(45) Date of Patent: Dec. 15, 2020

(54) ENGINEERED ALANYL-GLUTAMINE DIPEPTIDE BIOSYNTHETIC ENZYME AND APPLICATION THEREOF

(71) Applicant: INNOBIO CORPORATION LIMITED, Liaoning (CN)

(72) Inventors: Wenjie Yuan, Liaoning (CN); Chao Fan, Liaoning (CN); Yimin Li, Liaoning (CN); Hao Hong, Liaoning (CN); Wenzhong Wu, Liaoning (CN)

(73) Assignee: INNOBIO CORPORATION LIMITED, Liaoning (CN)

( * ) Notice: Subject to any disclaimer, the term of this patent is extended or adjusted under 35 U.S.C. 154(b) by 0 days.

(21) Appl. No.: 16/455,502

(22) Filed: Jun. 27, 2019

(65) Prior Publication Data
US 2019/0315801 A1 Oct. 17, 2019

Related U.S. Application Data

(63) Continuation-in-part of application No. PCT/CN2017/118167, filed on Dec. 25, 2017.

(30) Foreign Application Priority Data

Dec. 30, 2016 (CN) .......................... 2016 1 1254213
Dec. 30, 2016 (CN) .......................... 2016 1 1254240

(51) Int. Cl.
*C07K 5/06* (2006.01)
*C12N 1/16* (2006.01)
*C12N 1/20* (2006.01)

(52) U.S. Cl.
CPC .............. *C07K 5/06* (2013.01); *C12N 1/16* (2013.01); *C12N 1/20* (2013.01); *C12N 2500/32* (2013.01); *C12N 2500/34* (2013.01)

(58) Field of Classification Search
None
See application file for complete search history.

(56) References Cited

FOREIGN PATENT DOCUMENTS

| CN | 1150457 A | 5/1997 |
|---|---|---|
| CN | 1392156 A | 1/2003 |
| CN | 1671840 A | 9/2005 |
| CN | 104480075 A | 4/2015 |
| CN | 105274174 A | 1/2016 |
| CN | 106754447 A | 5/2017 |
| CN | 106754985 A | 5/2017 |

OTHER PUBLICATIONS

Abe et al. Biosci. Biotechnol. Biochem. 75 (11), 2087-2092 (2011) (Year: 2011).*
Bornscheuer et al. Curr Protoc Protein Sci. Nov. 2011;Chapter 26:Unit26.7. (Year: 2011).*
Wang et al. Biotechnol Lett. Jan. 2008;30(1):97-102. Epub Sep. 22, 2007 (Year: 2008).*
Accession AB610978. Nov. 30, 2011 (Year: 2011).*
Hirao, Yoshinori et al. "Enzymatic Production of L-Alanyl-L-glutamine by Recombinant *E. Coli* Expressing a-Amino Acid Ester Acyltransferase from Sphingobacterium siyangensis", Biosci. Biotechnol. Biochem., 2013, 618-623, vol. 77 issue 3, Research Institute for Bioscience Products and Fine Chemicals, Ajinomoto Co., Inc., 1-1 Suziki-cho, Kawasaki-ku, Kawasaki 210-8681, Japan.
Tabata, Kazuhiko et al. "Fermentative Production of L-Alanyl-L-Glutamine by a Metabolically Engineered *Escherichia coli* Strain Expressing L-Amino Acid a-Ligase" American Society for Microbiology, Oct. 2007, p. 6378-6385, vol. 73, No. 20, Tokyo BioFrontier Laboratories, Kyowa Hakko Kogyo Co. Ltd., 3-6-6 Ashahi-machi, Machida-shi, 194-8533 Tokyo, Japan, and Technical Research Laboratories, Kyowa Hakko Kogyo Co. Ltd., 1-1 Kyowa-cho, Hofu-shi, 747-8522 Yamaguchi, Japan.
He, Yanchun "Construction of a-Amino Acid Ester Acyltransferase Producing Recombinant *Escherichia coil* and Optimization of its Fermentation Conditions", Science-Engineering (A), China Master's Theses Full-Text Database, No. 12, Dec. 15, 2015 (Dec. 15, 2015), ISSN: 1674-0246.
Goffeau, A "*Saccharomyces cerevisiae* S288c flocculin FLO1, mRNA" Database Genbank [Online], Oct. 28, 2016, NM_001178230 (https://www.ncbi.nlm.nih.gov/ipg/?term=NM_001178230).
"X-Pro dipeptidyl-peptidase [*Sphingobacterium* sp. B29]" Database Genbank [Online], Jan. 19, 2017, WP_075991922 (https://www.ncbi.nlm.nih.gov/ipg/?term=WP_075991922).
Guo Tang, "Synthesis and Mechanism Studies on L-Alanyl-L-Gultamine", PhD thesis, Xiamen University, Jun. 2004.

* cited by examiner

*Primary Examiner* — Christian L Fronda
(74) *Attorney, Agent, or Firm* — Novick, Kim & Lee, PLLC; Allen Xue

(57) ABSTRACT

Provided is a gene encoding alanyl-glutamine dipeptide biosynthetic enzyme and the application thereof. The nucleotide sequence of said gene is shown in SEQ ID NO: 1. Further, provided is an amino acid sequence encoded by the gene, and provided recombinant vector, recombinant *E. coli*, recombinant *S. cerevisiae*, and a self-flocculating recombinant *S. cerevisiae* containing the gene. Furthermore, provided is a method for carrying out bioconversion to synthesize alanyl-glutamine dipeptide by using said recombinant microorganisms. The application of the gene and recombinant batteries has the characteristics of high molar conversion rate, fast production rate and repeated recycling of the bacteria. It is a good choice for efficient, environmentally friendly and economical production of alanyl-glutamine dipeptide. In addition, through the recycling process, it is expected to reduce the cost of industrial production, solve the problems of difficult enzyme recovery, low utilization rate and unstable enzyme activity.

11 Claims, 12 Drawing Sheets
Specification includes a Sequence Listing.

ENGINEERED ALANYL-GLUTAMINE DIPEPTIDE BIOSYNTHETIC ENZYME AND APPLICATION THEREOF

CROSS-REFERENCE TO RELATED APPLICATIONS

This application is a continuation-in-part of international application No. PCT/CN2017/118167 filed on Dec. 25, 2017, and claims priority to Chinese patent application Nos. 201611254213.2 and 201611254240.X filed on Dec. 30, 2016, and the entire disclosures of the foregoing applications are incorporated herein by reference.

INCORPORATION OF SEQUENCE LISTING

This application contains a sequence listing in Computer Readable Form (CRF). The CFR file containing the sequence listing entitled "8-PA251-0005-SequenceListing.txt", which was created on Jun. 27, 2019, and is 17,564 bytes in size. The information in the sequence listing is incorporated herein by reference in entirety.

TECHNICAL FIELD

The present invention relates to a biosynthesis method of alanyl-glutamine dipeptide, belonging to the biotechnological field.

BACKGROUND ART

Alanyl-glutamine dipeptide (L-Ala-Gln), also known as N(2)-L-alanyl-L-glutamine, has the advantages of high solubility, water solubility and high thermal stability, so it has gradually replaced glutamine (L-Gln) to become a main medicine for parenteral nutrition.

At present, the synthesis of alanyl-glutamine dipeptide mainly adopts chemical synthesis and biological enzyme catalysis methods. The chemical synthesis of alanyl-glutamine dipeptide includes a number of reaction steps, with many by-products, high toxicity of reagents and non-environmental friendliness (Tang Guo. Study on synthesis and reaction of N(2)-L-alanyl-L-glutamine dipeptide, Xiamen University, 2004; Chinese patent, method for synthesizing alanyl-glutamine dipeptide, CN1392156A).

However, the biological enzyme catalysis method also has the shortcomings such as high amount of enzyme, low productivity of peptide and only a part of higher hydrophobic amino acids synthesized, etc. CN104480075A and CN105274174A disclose two methods for synthesizing alanyl-glutamine dipeptide through catalyzation of biological enzymes, and a biological enzyme lyophilized powder or a biological enzyme buffer is used for catalytic reaction in the inventions, however, due to high cost for enzyme separation and purification and difficulty in recycling and reuse after reactions, it is not suitable for actual industrial production. Some researchers have acquired an amino acid ligase (Lal) from *Bacillus subtilis* that could synthesize a dipeptide using an unprotected amino acid as a substrate (CN1671840A). But the enzyme belongs to an ATP-dependent enzyme and needs to provide ATP exogenously, so the method has a high production cost and is unable to be used widely in the markets (Fermentative production of L-alanyl-L-glutamine by a metabolically engineered *Escherichia coli* strain expressing L-amino acid a-ligase. Applied and environmental microbiology, 2007, 73(20): 6378-6385).

SUMMARY OF THE INVENTION

An object of the present invention is to provide a complete technical solution for producing alanyl-glutamine dipeptide through biotransformation. By searching excellent exogenous genes encoding alanyl-glutamine dipeptide synthase, it is expected to construct recombinant engineered bacteria by genetic engineering and design a reasonable bio-fermentation engineering program to achieve green, efficient and low-cost industrial production of alanyl-glutamine dipeptide.

In order to achieve the foregoing object, the present invention first provides a gene encoding alanyl-glutamine dipeptide biosynthetic enzyme, and its nucleotide sequence is shown in SEQ ID NO: 1.

Second, the present invention provides an alanyl-glutamine dipeptide biosynthetic enzyme, which is encoded by the gene whose nucleotide sequence is SEQ ID NO: 1, and the amino acid sequence of the enzyme is shown in SEQ ID NO: 2.

The gene encoding alanyl-glutamine dipeptide biosynthetic enzyme has an excellent ability to promote conversion of substrate to alanyl-glutamine dipeptide. Further, in the present invention, the gene is used as a exogenous gene to construct a recombinant plasmid and a recombinant engineered strain by means of microbial engineering, and further the recombinant microorganism is used to directly catalyze the synthesis of alanyl-glutamine dipeptide in the fermentation system, to enhance the conversion efficiency of alanyl-glutamine dipeptide, and solve the shortcomings in the biotransformation engineering, such as difficult enzyme separation and purification, unstable enzyme activity and high cost.

In one aspect of applications, the present invention first provides a recombinant *E. coli*, and discloses a biosynthetic method of alanyl-glutamine dipeptide based on the recombinant *Escherichia coli*. The recombinant *E. coli* disclosed in the present invention is obtained by transferring a nucleotide sequence as shown in SEQ ID NO: 1 into *Escherichia coli*.

The biosynthesis method of alanyl-glutamine dipeptide based on the recombinant *Escherichia coli* comprises a step of transforming a substrate using the recombinant *E. coli*.

In another aspect of applications, the present invention discloses a recombinant *S. cerevisiae* comprising an exogenous gene having a nucleotide sequence such as SEQ ID NO: 1.

The recombinant *S. cerevisiae* prepared by the foregoing method can be used as a whole cell biocatalyst to efficiently and rapidly transform a substrate into an alanyl-glutamine dipeptide, without requiring a step of enzyme separation and purification. Based on this, it is still another object of the present invention to provide a biosynthesis method of alanyl-glutamine dipeptide, which comprises the step of transforming a substrate using the foregoing recombinant *S. cerevisiae* of the present invention.

Further, based on the provided recombinant *S. cerevisiae*, the present invention further discloses a recombinant *S. cerevisiae* having self-flocculation ability, and discloses a biosynthesis method for producing alanyl-glutamine dipeptide using the recombinant *S. cerevisiae*.

In summary, in the present invention, recombinant *E. coli* and recombinant *S. cerevisiae* are successfully constructed by the newly discovered transesterase and the gene encoding the enzyme by means of microbial engineering and enzyme genetic engineering, to transform substrate into alanyl-glutamine dipeptide by a whole cell biocatalyst, which omits the steps of enzyme separation and purification. It has the characteristics of high molar conversion rate, fast production rate and repeated recycling of the bacteria, so it is a good choice for efficient, environmentally friendly and economical production of alanyl-glutamine dipeptide. In addition, through the recycling process, it is expected to reduce the cost of industrial production, solve the problems of difficult enzyme recovery, low utilization rate and unstable enzyme activity, etc.

No matter what method for the production of alanyl-glutamine dipeptide is used in the present invention, it can achieve the following technical effects: first, the experimental raw materials are economical and easily available, the equipment is easy to operate and control, the whole cell catalytic synthesis route is simple and environmentally friendly, and the step of enzymatic separation and purification is omitted, reducing energy consumption and production cost; second, the reaction rate is fast, the reaction time is short, the molar conversion rate is high, the centrifugal reaction solution can terminate the reaction, the enzyme can be inactivated without heating, avoiding the toxic reactions of glutamine caused by high temperature; third, the bacterial cells are recycled, reducing the number of bacteria cultures, saving the cost of biological enzyme preparation and inactivation by heating, shortening the reaction cycle of alanyl-glutamine dipeptide, and increasing the production intensity, with obvious market competitiveness, thus, it is more suitable for the industrial production of alanyl-glutamine dipeptide.

BRIEF DESCRIPTION OF THE DRAWINGS 12 appended figures of the present invention:

DETAILED DESCRIPTIONS OF THE PREFERRED EMBODIMENTS

Figure 1:
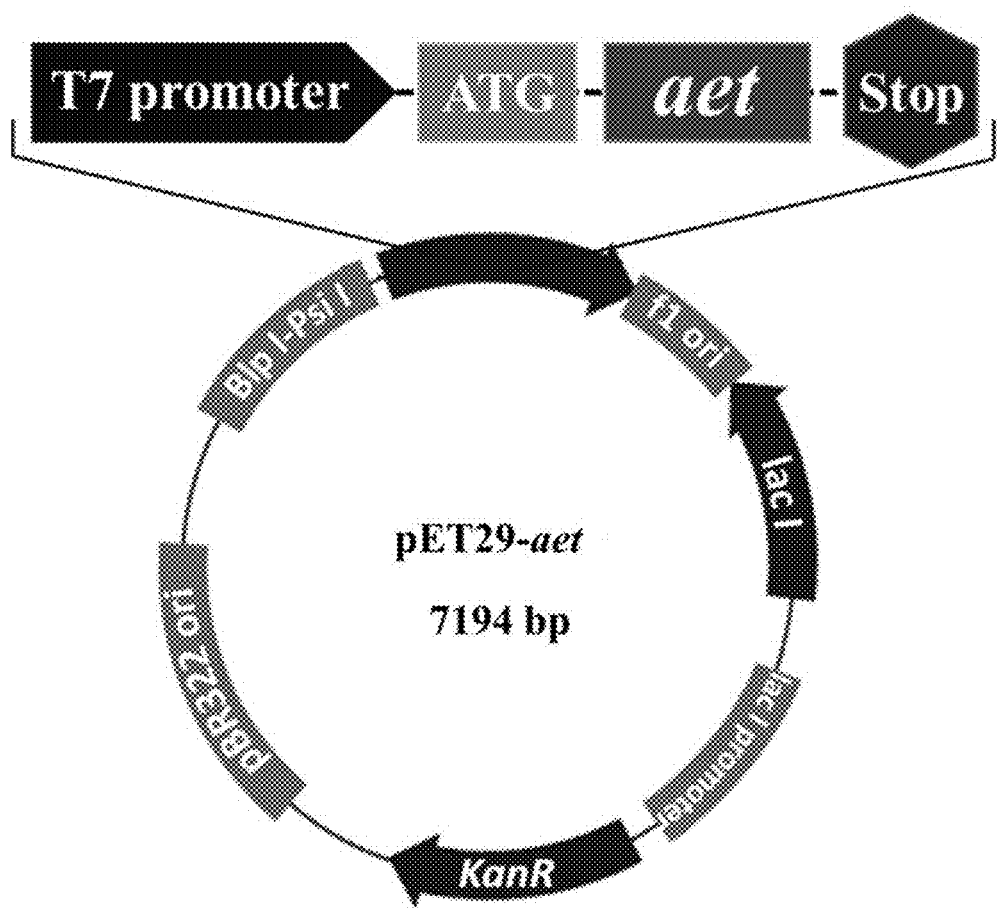
FIG. 1 is a schematic diagram showing the structure of a recombinant expression vector for recombinant *E. coli*.

The present invention first confirms that a gene encoding alanyl-glutamine dipeptide biosynthetic enzyme having a nucleotide sequence as shown in SEQ ID NO: 1 is obtained. The donor of this gene is a microorganism belonging to the genus *Sphingobacterium*, and more specifically, *Sphingobacterium siyangensis*.

An amino acid sequence encoded by the gene sequence of SEQ ID NO: 1 is shown in SEQ ID NO: 2. The amino acid sequence consists of 619 amino acids. Compared to the closest prior art (ZL03817916.4), there are changes of three amino acids: the amino acid at position 188 is changed from Y (tyrosine) to F (phenylalanine), both of which are aromatic amino acids, converted from an uncharged polar R-based amino acid to a non-polar R-based amino acid; amino acid 586/587: changed from AP (alanine/proline) to PS (proline/serine), which is converted from a neutral amino acid/heterocyclic amino acid to a heterocyclic amino acid/hydroxyl-containing amino acid, and also converted from a non-polar R-based amino acid to an uncharged polar R-based amino acid. Further enzyme functional domain analysis shows that transesterase mainly has two functional domains: Peptidase S15 (44-331) and PepX_C (382-613). Among them, Peptidase S15 (44-331) domain belongs to X-Prodipeptidyl-peptidase (S15 family), which is a key catalytic center of potential transesterase; while PepX_C (382-613) domain belongs to a C-terminal non-catalytic domain, but it has many similar structures to the dipeptidyl peptidase (the serine peptide exonuclease of the S9B protein family). Although its physiological functions need further research, two messages can be obtained from the prior art: protein dimerization is essential for the catalytic activity of the enzyme; glycosylation of the enzyme can affect its physiological function. In the present invention, the mutation of amino acid at the position 188 in the amino acid sequence of SEQ ID NO: 2 may change the catalytic domain of the enzyme; and amino acid mutation at position 586/587 may change the protein dimerization, and affect the catalysis activity of enzyme through them.

In the present information, after the information of biological enzyme gene is determined, plasmids are further amplified and preserved. Specifically, plasmids are amplified and preserved using *Escherichia coli* DH5a.

Based on this, in the present invention, a recombinant vector for different recombinant microorganisms and a recombinant microorganism are constructed using plasmids using the foregoing plasmid carrying the exogenous gene, and a method for producing alanyl-glutamine dipeptide by fermentation method using a recombinant microorganism is established.

One of the specific ways for the application of exogenous genes is to construct recombinant *E. coli* used for the biosynthesis of alanyl-glutamine dipeptide.

After digestion of the target gene and the expression vector, a recombinant vector for recombinant *E. coli* is recombinantly constructed, and a preferred vector is pET29a.

The constructed recombinant vector can be transformed into an expression host cell by a method in the prior art to construct a bioengineered bacteria carrying the target gene, and such a method can be exemplified but not limited to a heat shock method. The expression host selected in the present invention is *Escherichia coli*, including all *E. coli* which can be used as a transformation host according to the prior art, and preferably, but not limited to, E. coli BL21 (DE3).

The present invention provides a biosynthesis method for synthesis of alanyl-glutamine dipeptide synthesis based on the recombinant E. coli. In the method, at least a process of fermentation production by recombinant E. coli obtained from the foregoing method according to the prior art is included, which involves a step of transforming a substrate by the recombinant E. coli.

In the biosynthesis of alanyl-glutamine dipeptide, the substrate can be described as substrate comprising a carboxyl component and an amine component according to the prior art. In the present invention, the carboxyl component is selected from the group consisting of amino acid esters and amino acid amides, most preferably L-alanine methyl ester hydrochloride; the amine component is selected from the group consisting of amino acids, C-protected amino acids and amines, most preferably L-glutamine. The concentration of the substrate in the reaction system is established according to the proportional reaction relationship of the reactants, to facilitate the production most. The reaction concentration of substrate has no upper and lower limits. However, the highest reactant concentration is determined to some extent by the solubility of the reaction substrate in the system, and as the concentration of the reaction substrate increases, there is a certain degree of inhibition of conversion. In further detailed embodiments, the maximum solubility of glutamine is about 250 mM, but we can set the amount of reactants in the production according to a standard above it, for example, 600 mM that is used. At this time, a part of the original reaction system is in an insoluble solid state, but as the reaction continues, it can be gradually dissolved without affecting the progress of the transformation reaction. Therefore, the feeding method, on one hand, ensures the smooth progress of the reaction, and on the other hand, reduces the operation cost. As an operation mode which can be carried out, in the present invention, the concentrations of the carboxyl component and the amine component in the initial reaction system can be set to 50 to 600 mM.

In another aspect of the present invention, the method for synthesizing alanyl-glutamine dipeptide through biological conversion of recombinant E. coli, the pH of the conversion reaction system is 8.0 to 10.0, preferably 8.0 to 9.0.

In still another aspect of the present invention, in the method for synthesizing alanyl-glutamine dipeptide through biological conversion of recombinant E. coli, the amount of recombinant E. coli in the conversion reaction system is (system) OD 600=0.5-5.0.

According to the optimization results, one of the more specific embodiments of the foregoing biosynthesis method of alanyl-glutamine dipeptide using recombinant E. coli can be described as a method comprising the following steps:
(1) dissolving the substrate L-alanine methyl ester hydrochloride (L-Ala-OMe) and L-glutamine (L-Gln) in a buffer solution, and adjusting the pH to 8.0-10.0;
(2) adding the recombinant E. coli to a system obtained in step (1) to react, with the reaction temperature of 15 to 40° C., and pH of the reaction system of 8.0 to 10.0;
(3) collecting the reaction solution and centrifuging to separate bacterial cells and terminate the reaction at the reaction end point when pH is not lowered any longer.

In the detailed embodiment, the biosynthetic route of the alanyl-glutamine dipeptide of the present invention can be simply described as:

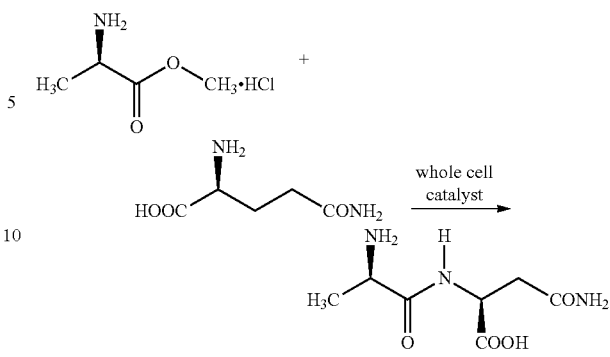

In the foregoing method description, on the one hand, the buffer solution described in the step (1) can be determined by those skilled in the art according to the prior art, preferably but not limited to the borate buffer; and in step (1), preferably the pH of alkali regulating system is 8.0 to 9.0. On the other hand, the reaction temperature described in the step (2) is preferably 25° C. Of course, temperature fluctuations within a certain range caused by the allowable measurement or control error are also acceptable; the pH of the reaction system in the step is still preferably 8.0-9.0.

Based on the foregoing described biosynthesis method of alanyl-glutamine dipeptide using recombinant E. coli, whole cells are used for production in the system synthesized by the catalytic reaction, the recombinant E. coli can be separately physically to terminate the reaction when the reaction proceeds to an appropriate extent, and the separated recombinant E. coli can be used as an engineered bacteria to be added to the biotransformation reaction system for recycling, therefore, in the most important embodiment of the method, a step of recycling the bacterial cells is further included. That is, the bacterial cells separated after termination of reactions in step (3) are added to a new reaction system for recycling.

In the following embodiments, the content and preferred mode of the present invention will be more completely and specifically explained. In the specific embodiment, the method for biosynthesizing the alanyl-glutamine dipeptide comprises the following steps:
(1) constructing a recombinant E. coli;
cloning a target gene with nucleotide sequence as SEQ ID NO: 1, constructing a recombinant vector comprising the gene using the expression vector pET29a, and transforming the recombinant vector into an expression host E. coli BL21 (DE3) by heat shock method;
(2) preserving the positive transformants obtained by the resistance gene screening, PCR and restriction enzyme verification step (1) in a slant medium;
The slant medium: yeast extract powder 5 g/L, tryptone 10 g/L, NaCl 10 g/L, agar powder 20 g/L, sterilized at 121° C. for 15 min, after cooling, adding kanamycin at a final concentration of 10-100 ug/mL;
(3) transferring activated recombinant E. coli to a seed culture medium at 37° C., 200 rpm overnight, and inoculating it into the fermentation medium at a certain inoculated dose for amplification culture; adding isopropyl thiogalactoside (IPTG) at a final concentration of 0.2 to 2.0 mM overnight to induce culture at a low temperature when cell $OD_{600}$=0.4 to 1.0;
The seed medium and the fermentation medium: yeast extract powder 5 g/L, tryptone 10 g/L, NaCl 10 g/L, sterilized at 121° C. for 15 min, after cooling, adding kanamycin at a final concentration of 10-100 ug/mL;

(4) Biosynthesis of alanyl-glutamine dipeptide: dissolving the substrate L-alanine methyl ester hydrochloride (L-Ala-OMe) and L-glutamine (L-Gln) in a buffer solution (the substrate concentration and the buffer type as claimed in claim 5), adding the culture of step (3), and adjusting the pH to 8.0-9.0, reacting the system at 25±1° C., until the pH value is no longer lowered as the end point of reaction, and collecting the reaction solution to centrifuge and separate bacterial cells;

(5) adding the bacterial cells obtained in the step (4) to a new reaction system for recycling production of alanyl-glutamine dipeptide.

The second specific method for the application of exogenous genes is to construct recombinant S. cerevisiae and use it for biosynthesis of alanyl-glutamine dipeptide.

Based on the preserved plasmid carrying the exogenous gene SEQ ID NO: 1, the target gene and the expression vector are digested and recombinantly constructed as a recombinant vector for recombinant S. cerevisiae, and the preferred vector is pYD1. The recombinant vector is then transformed into E. coli DH5a by particular ways not limited to a heat sock method. The transformants obtained in the above steps are then verified by ampicillin resistance gene screening, PCR and restriction enzyme digestion, and preserved in a slant medium. In order to obtain the desired recombinant S. cerevisiae, the recombinant expression vector ii is further extracted and transformed into S. cerevisiae competent cells, to obtain a positive transformant by deficient type screening. The positive transformant is activated and inoculated into the seed culture medium. When the bacterial cells are grown to $OD_{620}$=0.5-5.0, the bacterial cells are transferred to the induction medium to obtain a recombinant S. cerevisiae. In principle, the above S. cerevisiae competent cells include all SaccharomyceS. Cerevisiae competent cells which can be used as transformation hosts according to the prior art. In the particular embodiment, the expression host is SaccharomyceS. Cerevisiae EBY100. One of the prominent reasons for the selection of this host is that a yeast cell surface display technology can be used to fuse the transesterase protein to the yeast cell wall protein and anchor to the cell surface in the form of a native conformation, which is equivalent to the immobilization of the enzyme. Compared with the rest of the host expression, the display enzyme is easy to prepare, and the steps of enzyme separation and purification and immobilization are omitted, which helps to reduce the production cost of the enzyme preparation. Compared with intracellular enzymes, the display enzyme has no transmembrane resistance of substrate and product, and there is no degradation of the catalytic product alanyl-glutamine dipeptide by intracellular hydrolase.

Unless otherwise specified, the slant culture medium described in the present invention is prepared as follows: yeast extract powder 5.0 g/L, tryptone 10.0 g/L, NaCl 10.0 g/L, agar powder 20.0 g/L, sterilized at 121° C. for 15 min, and after cooling, ampicillin at a final concentration of 10 to 100 ug/mL is added.

The seed culture medium is prepared as follows: in 82 mL of ultrapure water, add 0.67 g of amino-free yeast nitrogen source; if a solid culture medium is prepared, add 3.0 g/L of agar powder, sterilize for 15 min at 121° C.; after sterilization, add 10 mL of amino acid mixture, 1 mL of leucine (6.0 g/L), 1 mL of histidine (2.0 g/L), 1 mL of threonine (20.0 g/L), and 5 mL of 40 wt % glucose;

The induction medium is prepared as follows: in 82 mL of ultrapure water, add 0.67 g of amino-free yeast nitrogen source; after sterilization, add 10 mL of amino acid mixture, 1 mL of leucine (6.0 g/L), 1 mL of histidine (2.0 g/L), 1 mL of threonine (20.0 g/L) and 5 mL of 40 wt % glucose;

The amino acid mixture described in the preparation of the foregoing seed and induction medium contains the following components: arginine 0.2 g/L, aspartic acid 1.0 g/L, glutamic acid 1.0 g/L, isoleucine acid 0.3 g/L, lysine 0.3 g/L, valine 1.5 g/L, methionine 0.2 g/L, phenylalanine 0.5 g/L, serine 3.75 g/L, tyrosine 0.3 g/L and adenine 0.4 g/L.

Based on the constructed recombinant S. cerevisiae, the present invention further provides a method for biosynthesizing alanyl-glutamine dipeptide which comprises the step of transforming a substrate using the above-described recombinant S. cerevisiae of the present invention.

In the biosynthesis of the alanyl-glutamine dipeptide using the recombinant S. cerevisiae, the substrate thereof can be described as substrate comprising a carboxyl component and an amine component according to the prior art. In the present invention, the carboxyl component is selected from the group consisting of amino acid esters and amino acid amides, most preferably L-alanine methyl ester hydrochloride; the amine component is selected from the group consisting of amino acids, C-protected amino acids and amines, preferably L-glutamine. The concentration of the substrate in the reaction system is established according to the proportional reaction relationship of the reactants, to facilitate the production most. The reaction concentration of substrate has no upper and lower limits. However, the highest reactant concentration is determined to some extent by the solubility of the reaction substrate in the system, and as the concentration of the reaction substrate increases, there is a certain degree of inhibition of conversion. In this detailed embodiment, the maximum solubility of glutamine is about 250 mM, but we can set the amount of reactants in the production according to a standard above it, for example, 600 mM that is used. At this time, a part of the original reaction system is in an insoluble solid state, but as the reaction continues, it can be gradually dissolved without affecting the progress of the transformation reaction. Therefore, the feeding method, on one hand, ensures the smooth progress of the reaction, and on the other hand, reduces the operation cost. In an operation mode which can be carried out, the concentrations of the carboxyl component and the amine component in the initial reaction system can be set to 100 to 600 mM.

In another aspect of the present invention, the method for synthesizing alanyl-glutamine dipeptide using recombinant S. cerevisiae, the pH of the conversion reaction system is 6.0 to 10.0, preferably 8.0 to 9.0. The temperature of the conversion reaction is 10 to 40° C., preferably 18 to 25° C., and most preferably 20 to 25° C.

In another aspect of the present invention, in the method for synthesizing alanyl-glutamine dipeptide using recombinant S. cerevisiae, the amount of using recombinant S. cerevisiae in the conversion reaction system is OD 600=0.5-5.0.

According to the optimization results, one of the more specific embodiments of the foregoing biosynthesis method of alanyl-glutamine dipeptide using recombinant S. cerevisiae can be described as a method comprising the following steps:

(1) dissolving the substrate L-alanine methyl ester hydrochloride (L-Ala-OMe) and L-glutamine (L-Gln) in a solvent solution, and adjusting the pH to 8.0-9.0;

(2) adding the recombinant *S. cerevisiae* to a system obtained in step (1) to react, with the reaction temperature of 10 to 40° C., and pH of the reaction system of 8.0 to 9.0;
(3) collecting the reaction solution to separate bacteria and terminate the reaction at the reaction end point when pH is not lowered any longer.

In a particular embodiment, the biosynthetic route of the alanyl-glutamine dipeptide of the present invention can be simply described as:

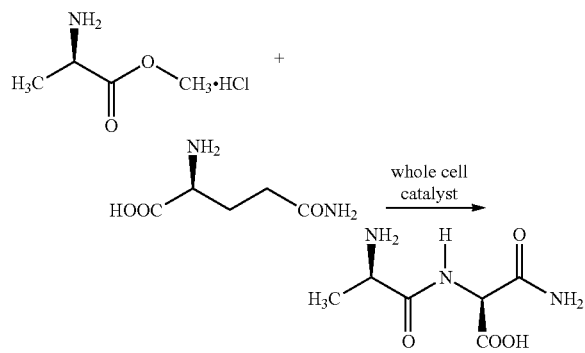

In the foregoing method description, on one hand, the buffer solution described in the step (1) can be determined by those skilled in the art according to the prior art, the solvent system can be water, a phosphate buffer or a borate buffer, preferably a phosphate buffer; and in step (1), preferably the pH of alkali regulating system is 8.0 to 9.0. On the other hand, the reaction temperature described in the step (2) is preferably 18 to 25° C., most preferably 20 to 25° C. Of course, temperature fluctuations within a certain range caused by the allowable measurement or control error are also acceptable; the pH of the reaction system in the step is still preferably 8.0-9.0.

Based on the foregoing described biosynthesis method of alanyl-glutamine dipeptide using recombinant *S. cerevisiae*, whole cells are used for production in the system synthesized by the catalytic reaction, the recombinant *S. cerevisiae* can be separately physically to terminate the reaction when the reaction proceeds to an appropriate extent, and the separated recombinant *S. cerevisiae* can be used as an engineered bacteria to be added to the biotransformation reaction system for recycling, therefore, in one most important embodiment of the method, a step of recycling the bacterial cells is further included. That is, the bacterial cells separated after termination of reactions in step (3) are added to a new reaction system for recycling.

In particular embodiments, due to the self-sedimentation characteristics of *SaccharomyceS. Cerevisiae* in the fermentation system, at the end of transformation reaction, the system is allowed to stand still, and the recombinant *S. cerevisiae* cells can be removed by the peristaltic pump after sedimentation; the resulting recombinant *S. cerevisiae* separated is used in the new reaction system.

In the following embodiments, the content and preferred mode of the present invention will be more completely and specifically explained. The method for biosynthesizing the alanyl-glutamine dipeptide using the recombinant *S. cerevisiae* comprises the following steps:
(1) constructing recombinant *S. cerevisiae*;
cloning a target gene with nucleotide sequence as SEQ ID NO: 1, constructing a recombinant vector comprising the gene using the expression vector pYD1, and transforming the recombinant vector into *E. coli* DH5α by heat shock method;
(2) preserving the transformants obtained by the ampicillin resistance gene screening, PCR and restriction enzyme verification step (1) in a slant medium;
The slant medium: yeast extract powder 5.0 g/L, tryptone 10.0 g/L, NaCl 10.0 g/L, agar powder 20.0 g/L, sterilized at 121° C. for 15 min, after cooling, adding ampicillin at a final concentration of 10-100 ug/mL;
(3) extracting a recombinant expression vector from the transformant obtained in the step (2), and transforming into *S. cerevisiae* EBY100 competent cells, to obtain positive transformant by deficient type screening. The positive transformant is activated and inoculated into a seed culture medium, and when the bacterial cells are grown to $OD_{620}=0.5$-5.0, they are transferred to an induction medium to obtain recombinant *SaccharomyceS. Cerevisiae*;
The seed culture medium: in 82 mL of ultrapure water, add 0.67 g of amino-free yeast nitrogen source; if a solid culture medium is prepared, add 3.0 g/L of agar powder, sterilize for 15 min at 121° C.; after sterilization, add 10 mL of amino acid mixture, 1 mL of leucine (6.0 g/L), 1 mL of histidine (2.0 g/L), 1 mL of threonine (20.0 g/L), and 5 mL of 40 wt % glucose;
The induction medium: in 82 mL of ultrapure water, add 0.67 g of amino-free yeast nitrogen source; sterilize for 15 min at 121° C.; after sterilization, add 10 mL of amino acid mixture, 1 mL of leucine (6.0 g/L), 1 mL of histidine (2.0 g/L), 1 mL of threonine (20.0 g/L), and 5 mL of 40 wt % galactose;
The amino acid mixture described above in the preparation of the seed and induction medium contains the following components: arginine 0.2 g/L, aspartic acid 1.0 g/L, glutamic acid 1.0 g/L, isoleucine 0.3 g/L, lysine 0.3 g/L, valine 1.5 g/L, methionine 0.2 g/L, phenylalanine 0.5 g/L, serine 3.75 g/L, tyrosine 0.3 g/L and adenine 0.4 g/L.
(4) Biosynthesis of alanyl-glutamine dipeptide: dissolve the substrate L-alanine methyl ester hydrochloride (L-Ala-OMe) and L-glutamine (L-Gln) in a solvent system, add a culture in the step (3) to adjust to pH of 8.0 to 9.0 and react the system at a condition of 20±5° C. until the end point of reactions when the pH value is not lowered any longer, and collect reaction liquid to separate bacterial cells;
(5) adding the bacterial cells obtained in the step (4) to a new reaction system for recycling production of alanyl-glutamine dipeptide.

In a third embodiment of exogenous gene application, a recombinant *S. cerevisiae* having self-flocculating ability is further constructed based on the constructed recombinant *SaccharomyceS. Cerevisiae*.

The recombinant *S. cerevisiae* having self-flocculating ability is one of the preferred embodiments of the above recombinant *S. cerevisiae*, further comprising an exogenous flocculating gene FLO1.

The described recombinant *S. cerevisiae* with self-flocculating ability can be constructed by the following method:
(1) amplifying a flocculating gene FLO1 having a nucleotide sequence of SEQ ID NO: 8 using a primer pair in which a nucleotide sequence is SEQ ID NO: 6/7.
(2) ligating the amplified product to the expression vector pRS425-pGK, and transforming the ligated product into *E. coli* DH5a competent cells, and screening transformants on the LB resistant medium plate and perform verification, to obtain a self-flocculating recombinant vector;
(3) transforming the self-flocculating recombinant vector into the competent cells of the foregoing recombinant *S.* cerevisiae of the present invention, to obtain a recombinant S. cerevisiae with self-flocculating ability by LEU-deficient screening (self-flocculating recombinant S. cerevisiae).

Further, the present invention further provides another method of biosynthesizing alanyl-glutamine dipeptide based on the obtained self-flocculating, comprising the following steps:

(1) constructing a recombinant S. cerevisiae;
cloning a target gene with nucleotide sequence as SEQ ID NO: 1, constructing a recombinant vector comprising the gene using the expression vector pYD1, and transforming the recombinant vector into E. coli DH5α by heat shock method;

(2) preserving the transformants obtained by the ampicillin resistance gene screening, PCR and restriction enzyme verification step (1) in a slant medium;

(3) extracting a recombinant expression vector from the transformant obtained in the step (2), and transforming into S. cerevisiae EBY100 competent cells, to obtain positive transformant by deficient type screening. The positive transformant is activated and inoculated into a seed culture medium, and when the bacterial cells are grown to $OD_{620}$=0.5-5.0, they are transferred to an induction medium to obtain recombinant SaccharomyceS. Cerevisiae;

(4) amplifying a flocculating gene FLO1 having a nucleotide sequence of SEQ ID NO: 8 using a primer pair with a nucleotide sequence of SEQ ID NO: 6/7.

(5) ligating the amplified product obtained in step (4) to the expression vector pRS425-pGK, and transforming the ligated product into E. coli DH5a competent cells, and screening transformants on the LB resistant medium plate and perform verification, to obtain a self-flocculating recombinant vector;

(6) transforming the self-flocculating recombinant vector into the competent cells of the recombinant S. cerevisiae prepared in the step (3), to obtain a recombinant S. cerevisiae with self-flocculating ability by LEU-deficient screening.

(7) Biosynthesis of alanyl-glutamine dipeptide:
dissolving the substrate L-alanine methyl ester hydrochloride and L-glutamine in a solvent system, adding the recombinant S. cerevisiae with self-flocculating ability in step (6), and adjusting the pH to 8.0-9.0, reacting the system at 20±5° C., until the pH value is no longer lowered as the end point of reaction, and collecting the reaction solution to separate bacterial cells;

(8) adding the bacterial cells obtained in the step (7) to a new reaction system for recycling production of alanyl-glutamine dipeptide.

The following non-limiting examples are intended to be illustrative of the invention and are not to be construed as limiting the present invention in any way.

Example 1

Construction of Recombinant E. coli:

The primer (SEQ ID NO: 3/4) was designed according to the known related enzyme sequence (SEQ ID NO: 5), and the biological enzyme gene SEQ ID NO: 1 was amplified using Sphingobacterium siyangensis genome (strain No.: 1.6855) from General Collection of Chinese Microorganisms as a template.

Among them, PCR reaction system: dNTPs (2.5 mM each), 4 µL; 10*Buffer, 5 uL; F (10 µM), 2 µL; R (10 µM), 2 µL; ExTaq enzyme (5 U/µL), 1 µL; ddH2O, 34 µL.

PCR reaction conditions: 94° C., 5 min, 1 cycle; 94° C., 30 sec, 55° C., 30 sec, 72° C., 2 min, 30 cycles; 72° C., 7 min, 1 cycle. The product was stored at 4° C.

The PCR product was purified by gel recovery, and ligated with the plasmid pMD™19-T. After extraction of plasmid, the positive clone was sequenced. The bio-enzyme gene obtained by restriction enzyme digestion was ligated with the expression vector pET29a after the same treatment, and the ligated product was transformed into E. coli DH5a competent cells, cultured on LB resistant medium. Single colonies were picked up, and plasmids were digested and identified and subjected to DNA sequencing to obtain a biological enzyme expression vector. Then, it was transformed into the expression host competent cells by heat shock method, to obtain a recombinant E. coli capable of catalyzing the synthesis of alanyl-glutamine dipeptide.

Example 2

Fermentation Culture of Recombinant E. coli:

The recombinant E. coli was inoculated into a LB liquid medium (yeast extract powder 5 g/L, tryptone 10 g/L, NaCl 110 g/L), and bacterial cells were activated at 37° C., 200 rpm. Thereafter, cells were transferred to a seed culture medium, and cultured while shaking at 37° C., 200 rpm overnight. The cells were inoculated to 1.5 L of the fermentation medium at an inoculated dose of 1%. After cells were incubated at 37° C., 200 rpm to OD 620=0.6 to 0.8 by introducing air, the inductive agent IPTG was added overnight, centrifuged to collect bacterial cells as the recombinant E. coli as described in the remaining embodiments of the present invention.

Example 3

Synthesis of Alanyl-Glutamine Dipeptide by Catalyzing Whole Cells at a Concentration of Substrate of 50 mM:

0.698 g of L-alanine methyl ester hydrochloride (50 mM L-Ala-OMe) and 1.462 g of L-glutamine (100 mM L-Gln) were weighed and dissolved in 90 mL of 0.2 M pH 8.7 borate buffer solution, and temperature was controlled at 25° C. and the pH was adjusted to 8.5 with a 6 M aqueous NaOH solution. Recombinant E. coli was added to the reaction system, $OD_{600}$=0.75, pH was stabilized with 6 M NaOH solution, and after 10 min, the cells were removed by centrifugation to terminate the reaction. The highest concentration of alanyl-glutamine dipeptide was 9.04 g/L and the molar conversion rate was 83.3% measured by high performance liquid chromatography (Appendix V D, part II, Chinese Pharmacopoeia, 2010 edition).

Example 4

Synthesis of Alanyl-Glutamine Dipeptide by Catalyzing Whole Cells at a Concentration of Substrate of 100 mM:

1.396 g of L-alanine methyl ester hydrochloride (100 mM L-Ala-OMe) and 1.462 g of L-glutamine (100 mM L-Gln) were weighed and dissolved in 90 mL of 0.2 M pH 8.7 borate buffer solution, and temperature was controlled at 25° C. and the pH was adjusted to 8.5 with a 6 M aqueous NaOH solution. Recombinant E. coli was added to the reaction system, $OD_{600}$=2.0, pH was stabilized with 6 M NaOH solution, and after 10 min, the cells were removed by centrifugation to terminate the reaction. The highest concentration of alanyl-glutamine dipeptide was 15.92 g/L

Example 5

Synthesis of Alanyl-Glutamine Dipeptide by Catalyzing Whole Cells at a Concentration of Substrate of 200 mM:

2.792 g of L-alanine methyl ester hydrochloride (200 mM L-Ala-OMe) and 2.924 g of L-glutamine (200 mM L-Gln) were weighed and dissolved in 90 mL of 0.2 M pH 8.7 borate buffer solution, and temperature was controlled at 25° C. and the pH was adjusted to 8.5 with a 6 M aqueous NaOH solution. Recombinant E. coli was added to the reaction system, $OD_{600}$=2.0, pH was stabilized with 6 M NaOH solution, and after 10 min, the cells were removed by centrifugation to terminate the reaction. The highest concentration of alanyl-glutamine dipeptide was 31.34 g/L measured by high performance liquid chromatography.

Example 6

Synthesis of Alanyl-Glutamine Dipeptide by Catalyzing Whole Cells at a Concentration of Substrate of 400 mM:

5.584 g of L-alanine methyl ester hydrochloride (200 mM L-Ala-OMe) and 5.848 g of L-glutamine (400 mM L-Gln) were weighed and dissolved in 90 mL of 0.2 M pH 8.7 borate buffer solution, and temperature was controlled at 25° C. and the pH was adjusted to 8.5 with a 6 M aqueous NaOH solution. Recombinant E. coli was added to the reaction system, $OD_{600}$=2.0, pH was stabilized with 6 M NaOH solution, and after 20 min, the cells were removed by centrifugation to terminate the reaction. The highest concentration of alanyl-glutamine dipeptide was 61.53 g/L measured by high performance liquid chromatography.

Example 7

Synthesis of Alanyl-Glutamine Dipeptide by Catalyzing Whole Cells at a Concentration of Substrate of 600 mM:

8.376 g of L-alanine methyl ester hydrochloride (600 mM L-Ala-OMe) and 8.772 g of L-glutamine (600 mM L-Gln) were weighed and dissolved in 90 mL of 0.2 M pH 8.7 borate buffer solution, and temperature was controlled at 25° C. and the pH was adjusted to 8.5 with a 6 M aqueous NaOH solution. Recombinant E. coli was added to the reaction system, $OD_{600}$=2.0, pH was stabilized with 6 M NaOH solution, and after 20 min, the cells were removed by centrifugation to terminate the reaction. The highest concentration of alanyl-glutamine dipeptide was 79.91 g/L measured by high performance liquid chromatography (Appendix V D, part II, Chinese Pharmacopoeia, 2010 edition).

Example 8

Figure 2:
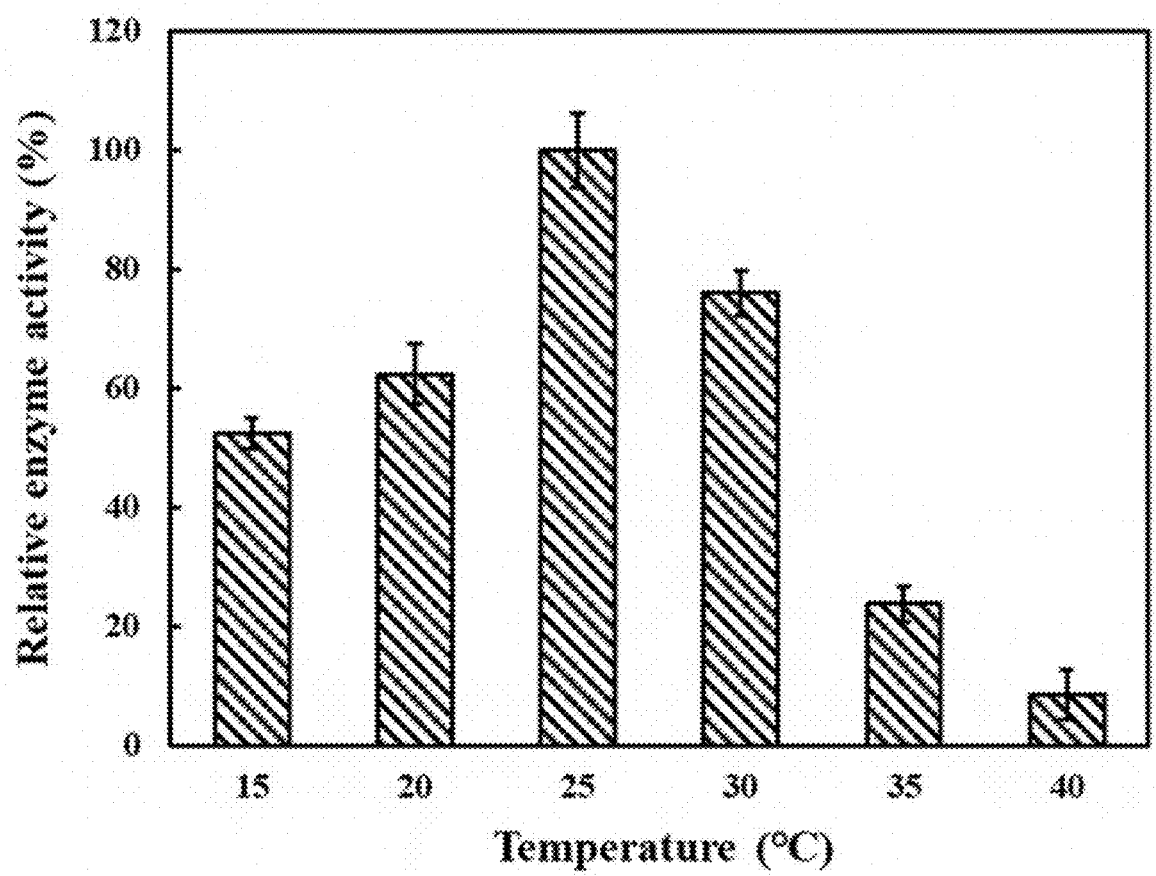
FIG. 2 is a graph showing the relative enzymatic activity of a recombinant *E. coli* with the reaction temperature.

Effects of Different Reaction Temperatures on Whole-Cell Catalytic Synthesis of Alanyl-Glutamine Dipeptide:

Recombinant E. coli was inoculated to the LB fermentation medium at an inoculated dose of 1%, and the cells were cultured to OD 620=0.73 at 200 rpm at 37° C. by introducing air, then the inductive agent IPTG was added to induce expression of biological enzymes. The cells were collected by centrifugation for alanyl-glutamine dipeptide catalysis. 5.584 g of L-alanine methyl ester hydrochloride (400 mM L-Ala-OMe) and 5.848 g of L-glutamine (400 mM L-Gln) were weighed and dissolved in 90 mL of 0.2 M pH 8.7 borate buffer solution, adjusted to pH 8.5 with a 6 M NaOH solution, and then catalytic synthesis reactions were carried out at different reaction temperatures. The concentration of alanyl-glutamine dipeptide was determined by high performance liquid chromatography (Appendix V D, part II, Chinese Pharmacopoeia, 2010 edition). The recombinant E. coli whole cells could catalyze the synthesis of alanyl-glutamine dipeptide within the range of 15-40° C. The yield of alanyl-glutamine dipeptide catalyzed and synthesized by whole cells at 25° C. was highest, using the enzyme activity as 100%, the relative enzymatic activity at different temperatures was plotted, as shown in FIG. 2.

Example 9

High-Efficiency Synthesis of Alanyl-Glutamine Dipeptide by Recycling of Bacterial Cells:

The culture of recombinant E. coli was carried out according to the same procedure as described in Example 2. The collected bacterial cells were subjected to catalytic synthesis reaction according to Example 3. When the reaction was terminated, the concentration of alanyl-glutamine dipeptide was measured by high performance liquid chromatography (Appendix V D, part II, Chinese Pharmacopoeia, 2010 edition), with a corresponding enzyme activity of 100%.

Figure 3:
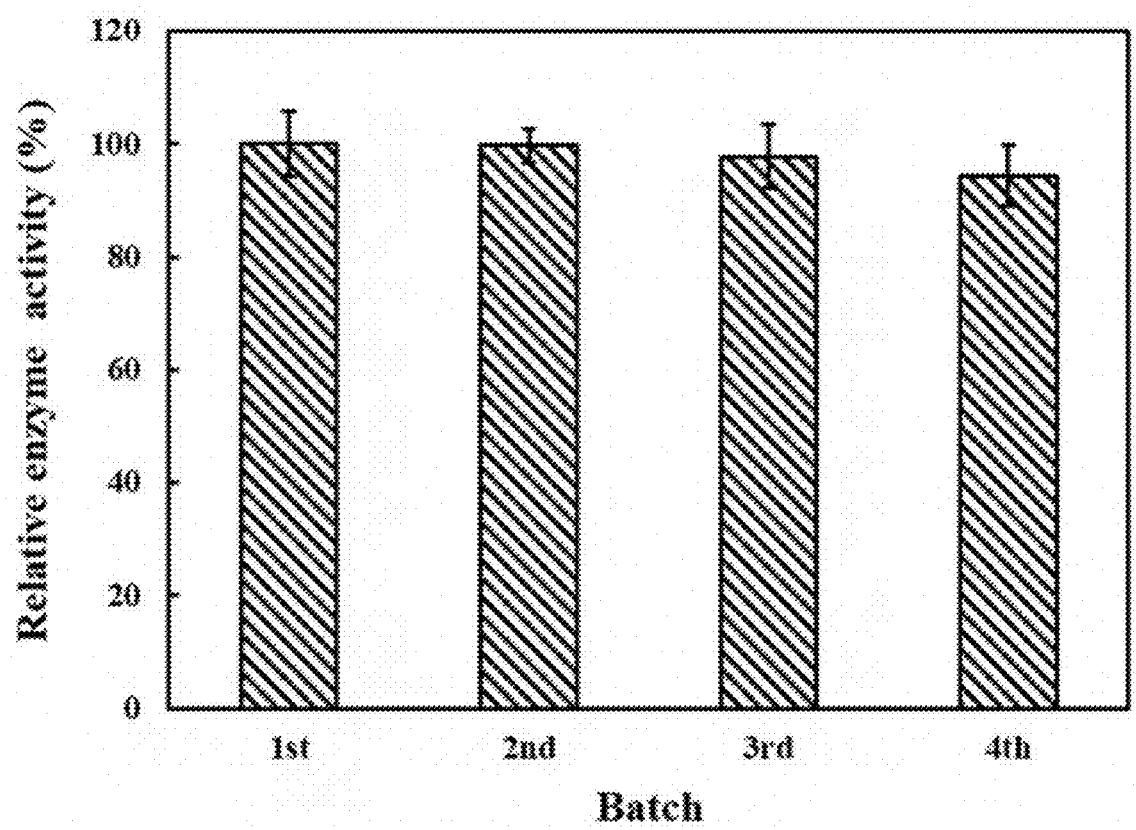
FIG. 3 is a graph showing change of the relative enzyme activity of a recombinant *E. coli* with the number of times of recycling.

The bacterial cells were collected by centrifugation as the next cycle of engineered bacteria, and the foregoing reaction process was repeated. The relative enzyme activity of bacterial cells in the first cycle was calculated as 99.8%, and that in the second cycle and the third cycle was 97.8% and 94.4% respectively, as shown in FIG. 3. As there was a small loss of cells during centrifugation and recovery of bacterial cells, the enzymatic activity of the alanyl-glutamine dipeptide catalyzed by the recombinant E. coli cells for repeated cycles was stable, suitable for industrial production.

Example 10

Comparison with the Prior Art:

Japan Ajinomoto Corporation (patent ZL03817916.4) is leading in the biosafety, conversion efficiency and productivity of transesterases used in the field of enzymatic synthesis of alanyl-glutamine dipeptide in the world. (Biosci Biotechnol Biochem. 2013; 77(3): 618-23; 2011; 75 (11): 2087-2092) The optimal result reported in the literature was as follows: when the cell $OD_{610}$ was about 4.6 in the reaction system, the molar conversion of two kinds of substrate was 67%, but the catalytic reaction time was longer, 40 min. In contrast, the transesterase expression system constructed in the present invention had a molar conversion rate of 83.3% within 10 min under the reaction condition of cell volume $OD_{600}$ at 0.75, which had faster production efficiency and higher molar conversion rate.

More detailed comparative data were described in Table 1 (data sources of Japan Ajinomoto: Enzymatic production of L-Alany-L-glutamine by recombinant E. coli expressing a-Amino acid ester Acyltransferase from Sphingobacterium siyangensis. Bioscience, biotechnology, and biochemistry, 2013, 77(3): 618-623). As shown from the results, under similar substrate conditions, the present invention can achieve more excellent conversion rate within a time period far less than the reaction time of the prior art ZL03817916.4. Therefore, the cell enzymes of the present invention have stronger catalytic activities.

TABLE 1

| Parameters | Prior art | The present invention | |
|---|---|---|---|
| Substrate concentration (mM) | 524 | 600 | 400 |
| Reaction time (min) | 40 | 30 | 20 |
| Reaction temperature (° C.) | 25 | 25 | 25 |
| pH | 8.5 | 8.5 | 8.5 |
| Cell concentration (OD) | 4.8 | 2.4 | 2.4 |
| Product concentration (mM) | 321 | 368 | 283 |
| Molar conversion rate (%) | 67% | 61% | 71% |
| Concentration (g/L) | 69.7 | 79.9 | 61.5 |
| Productivity (g/L · min$^{-1}$) | 1.7425 | 2.66 | 3.075 |

Example 11

Construction of Recombinant S. cerevisiae:

The exogenous enzyme gene (SEQ ID NO: 1) was amplified in the same manner as that in Example 1.

After the end of the PCR reaction, 2 μL of PCR product was detected by agarose gel electrophoresis, and the amplified PCR product was purified by PCR product purification kit (OMEGA, USA) and stored in a refrigerator at −20° C. for standby use.

Figure 4:
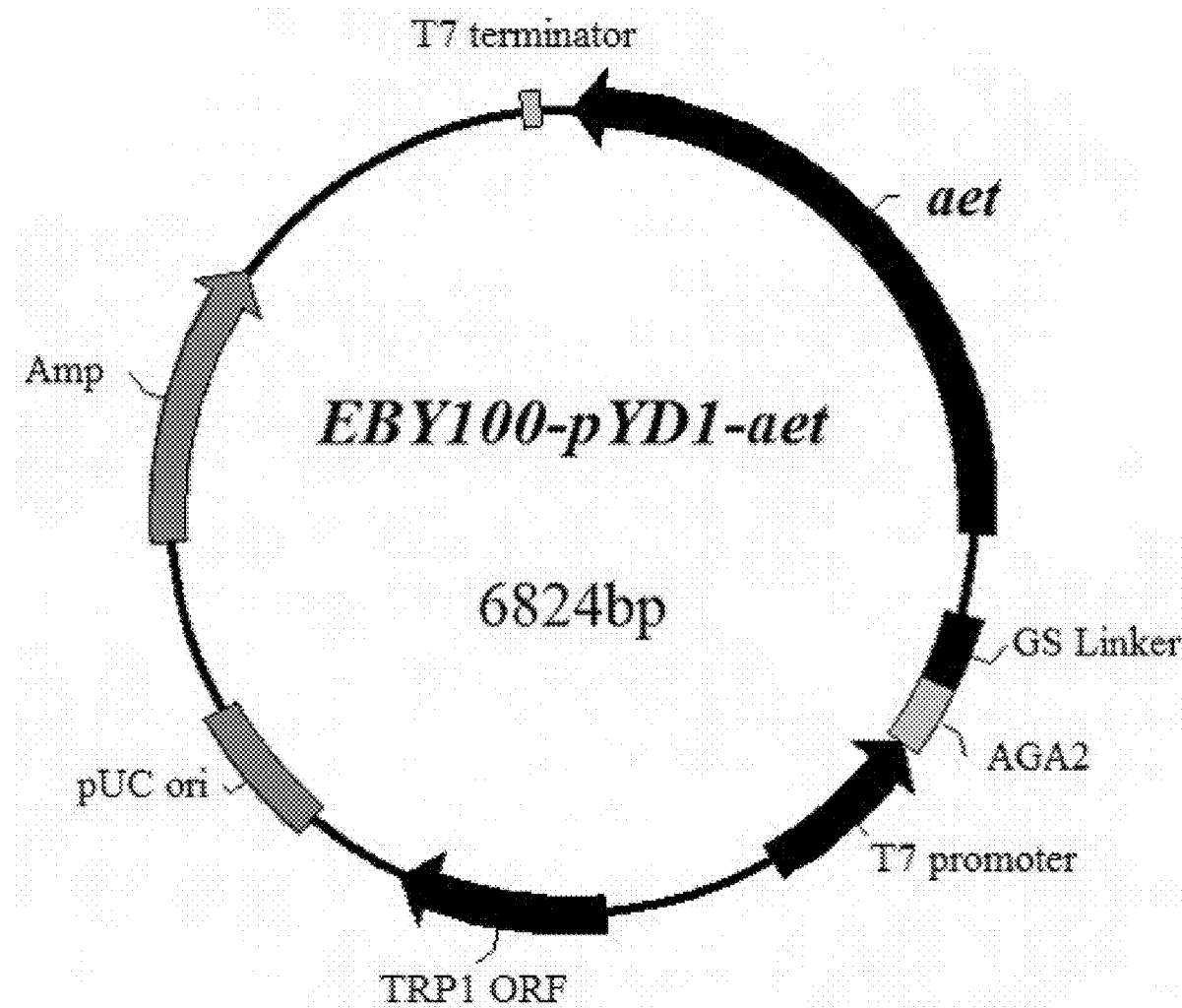
FIG. 4 is a schematic diagram showing the structure of a recombinant expression vector for recombinant *S. cerevisiae*.

The PCR product and the expression vector pYD1 were digested and ligated overnight, and the ligated product was transformed into E. coli DH 5a competent cells, and the transformants were screened on a plate of LB resistant medium (the medium composition was the same as that of the slant medium), and then PCR and restriction enzyme digestion and DNA sequencing were performed separately. The yeast recombinant expression vector was obtained after verification, as shown in FIG. 4, and then deficient type screening was performed to obtain a recombinant S. cerevisiae capable of catalyzing the synthesis of alanyl-glutamine dipeptide, as the recombinant S. cerevisiae used in the remaining examples of the present invention.

Example 12

Fermentation Culture of Recombinant S. cerevisiae:

Recombinant S. cerevisiae was inoculated into a seed medium, and the bacterial cells were activated at 30° C. and 180 rpm. Thereafter, the cells were transferred to a seed culture medium for amplification culture, and cultured while shaking at 30° C. and 180 rpm. When growing to an appropriate amount, cells were inoculated into 1.0 L induction medium for culture while introducing air at 20° C., 150 rpm. 16-24 h later, cells were centrifuged and collected, as the recombinant S. cerevisiae as described in the present invention.

Example 13

Verification of Surface Display Bioenzyme:
a. Recombinant S. cerevisiae cultured in Example 12 was centrifuged to collect cells at 3000 to 5000 rpm, and washed twice with phosphate buffer;
b. The supernatant was discharged and the cells were resuspended in phosphate buffer containing 1 mg/mL bovine serum albumin (BSA) and 1 μg antibody (anti-V5-FITC);
c. After placed on ice for 30 min, cells were collected by centrifugation at 3000-5000 rpm and washed twice with phosphate buffer;
d. Finally, the cells were resuspended in phosphate buffer and observed under a fluorescent inverted microscope and laser confocal microscope.

When the biological enzyme was displayed on the cell surface, the exposed V5 epitope can specifically bind to the free fluorescein-labeled antibody in assay b, and then the cells were washed with phosphate buffer to remove excessive and non-specifically bound antibodies. Finally, the fluorescent signals were detected at the excitation wavelength of 493 nm, which was the fluorescent signal generated by specific binding, demonstrating that the biological enzyme was successfully displayed on the cell surface.

The phosphate buffer solution described in this example contained 137 mM sodium chloride; 2.7 mM potassium chloride; 10 mM phosphate, and buffer solution with pH 7.4.

Figure 5:
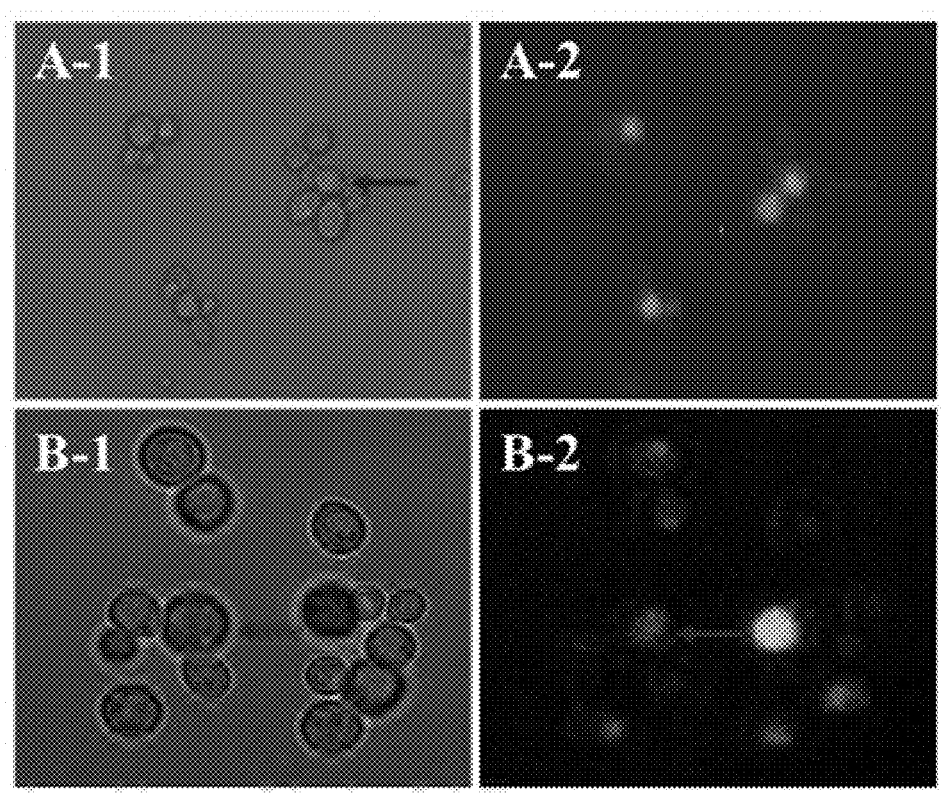
FIG. 5 is a fluorescent and laser confocal verification map of a bioenzyme on the surface of recombinant *S. cerevisiae* cells.

Fluorescence signals detected under fluorescence inverted microscope and laser confocal microscope respectively were shown in FIG. 5 (A-1/A-2 was the verification result of fluorescence inverted microscope; B-1/B-2 was the verification result of laser confocal microscope). Among them, Figure A-1/B-1 was the cell position chart under white light; Figure A-2/B-2 was the fluorescence signal diagram of the cells at the excitation wavelength of 493 nm. It could be shown that cells that could produce green fluorescent signals existed in the same position, demonstrating that the biological enzymes had been displayed on the cell surface.

The biological enzymes were displayed on the cell surface to achieve immobilization of enzymes. Firstly, it overcame the effect of substrate and product transmembrane resistance and increased the reaction rate; secondly, compared with intracellular enzymes, on one hand, it avoided the hydrolysis of intracellular protease and peptidase, to facilitate to maintain the stability of enzyme activity and accumulate the product. On the other hand, in the process of enriching the enzyme, the steps of cell breaking and enzyme separation and purification were omitted, and the production cost was reduced to enhance the economic benefit; finally, with the repeated use of cells, the reuse of enzymes was achieved, to solve the problems of difficulty in enzyme recovery and high cost.

Example 14

Study on Catalytic Synthesis of Alanyl-Glutamine Dipeptide by Yeast Whole Cells at a Concentration of Substrate of 100 mM.

Figure 6:
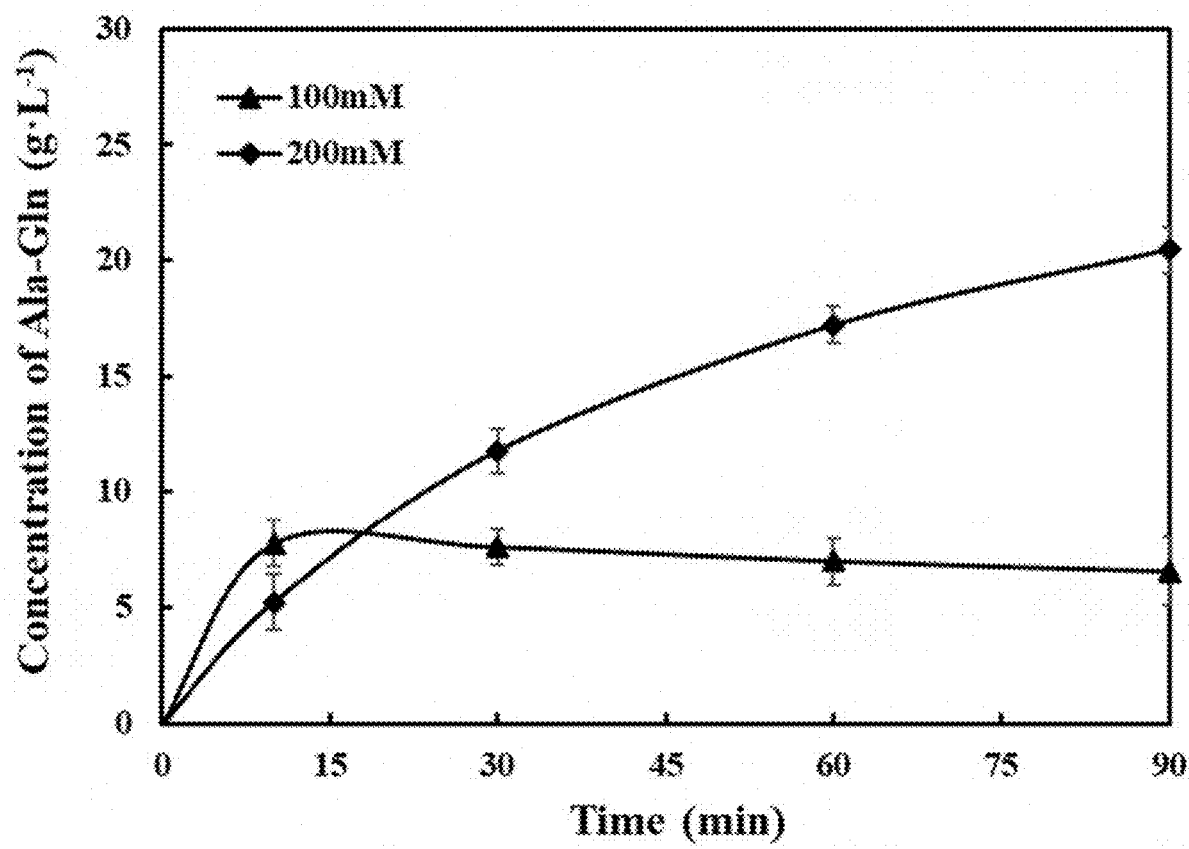
FIG. 6 is a graph showing the effect of different substrate concentrations on the whole-cell catalytic synthesis of alanyl-glutamine dipeptide by recombinant *S. cerevisiae*.

1.396 g of L-alanine methyl ester hydrochloride (100 mM L-Ala-OMe) and 1.462 g of L-glutamine (100 mM L-Gln) were weighed and dissolved in 90 mL of water at a controlled temperature of 25° C., and the solution was adjusted to pH 8.5 with 6 M NaOH solution, and then sample application was performed and stored at 4° C. The recombinant S. cerevisiae was added to the reaction system to make $OD_{620}$=0.5-5.0 in the reaction solution, and the pH was kept stable with 6M NaOH solution. At the end of the reaction, the solution was centrifuged and the supernatant was stored at 4° C. The highest concentration of alanyl-glutamine dipeptide within the reaction time was 7.7 g/L measured by high performance liquid chromatography (Appendix V D, part II, Chinese Pharmacopoeia, 2010 edition), as shown in FIG. 6.

Example 15

Study on Catalytic Synthesis of Alanyl-Glutamine Dipeptide by Yeast Whole Cells at a Concentration of Substrate of 200 mM 2.792 g of L-alanine methyl ester hydrochloride (200 mM L-Ala-OMe) and 2.924 g of L-glutamine (200 mM L-Gln) were weighed and dissolved in 90 mL of water at a controlled temperature of 25° C., and the solution was adjusted to pH 8.5 with 6 M NaOH solution, and then sample application was performed and stored at 4° C. The recombinant S. cerevisiae was added to the reaction system to make $OD_{620}$=0.5-5.0 in the reaction solution, and the pH was kept stable with 6M NaOH solution. At the end of the reaction, the solution was centrifuged and the supernatant was stored at 4° C. The highest concentration of alanyl-glutamine dipeptide within the reaction time was 20.4 g/L measured by high performance liquid chromatography (Appendix V D, part II, Chinese Pharmacopoeia, 2010 edition), as shown in FIG. 6.

Example 16

Study on Catalytic Synthesis of Alanyl-Glutamine Dipeptide by Yeast Whole Cells Under the Condition of (50 mM L-Ala-OMe, 100 mM L-Gln):

0.698 g of L-alanine methyl ester hydrochloride (50 mM L-Ala-OMe) and 1.462 g of L-glutamine (100 mM L-Gln) were weighed and dissolved in 90 mL of 0.2 M pH 8.7 phosphate buffer solution at a controlled temperature of 20° C., and the solution was adjusted to pH 8.5 with 6 M NaOH solution, and then sample application was performed and stored at 4° C. The recombinant S. cerevisiae was added to the reaction system to make $OD_{620}$=0.5-5.0 in the reaction solution, and the pH was kept stable with 6M NaOH solution, to react 20 min. After centrifugation, the supernatant was stored at 4° C. The concentration of alanyl-glutamine dipeptide within the reaction time was 5.8 g/L measured by high performance liquid chromatography (Appendix V D, part II, Chinese Pharmacopoeia, 2010 edition).

Example 17

Study on Catalytic Synthesis of Alanyl-Glutamine Dipeptide by Yeast Whole Cells Under the Condition of (100 mM L-Ala-OMe, 200 mM L-Gln):

1.396 g of L-alanine methyl ester hydrochloride (100 mM L-Ala-OMe) and 2.924 g of L-glutamine (200 mM L-Gln) were weighed and dissolved in 90 mL of 0.2 M pH 8.7 phosphate buffer solution at a controlled temperature of 20° C., and the solution was adjusted to pH 8.5 with 6 M NaOH solution, and then sample application was performed and stored at 4° C. The recombinant S. cerevisiae was added to the reaction system to make $OD_{620}$=0.5-5.0 in the reaction solution, and the pH was kept stable with 6M NaOH solution, to react 40 min. After centrifugation, the supernatant was stored at 4° C. The concentration of alanyl-glutamine dipeptide within the reaction time was 14.4 g/L measured by high performance liquid chromatography (Appendix V D, part II, Chinese Pharmacopoeia, 2010 edition).

Example 18

Study on Catalytic Synthesis of Alanyl-Glutamine Dipeptide by Yeast Whole Cells Under the Condition of (200 mM L-Ala-OMe, 400 mM L-Gln):

2.792 g of L-alanine methyl ester hydrochloride (200 mM L-Ala-OMe) and 5.848 g of L-glutamine (400 mM L-Gln) were weighed and dissolved in 90 mL of 0.2 M pH 8.7 phosphate buffer solution at a controlled temperature of 20° C., and the solution was adjusted to pH 8.5 with 6 M NaOH solution, and then sample application was performed and stored at 4° C. The recombinant S. cerevisiae was added to the reaction system to make $OD_{620}$=0.5-5.0 in the reaction solution, and the pH was kept stable with 6M NaOH solution, to react 60 min. After centrifugation, the supernatant was stored at 4° C. The concentration of alanyl-glutamine dipeptide within the reaction time was 24.7 g/L measured by high performance liquid chromatography (Appendix V D, part II, Chinese Pharmacopoeia, 2010 edition).

Example 19

Effect of Different Reaction Systems on Catalytic Synthesis of Alanyl-Glutamine Dipeptide by Yeast Whole Cells The recombinant S. cerevisiae was cultured in the same manner as that in Example 12, and cells were collected by centrifugation for alanyl-glutamine dipeptide catalytic reaction. The effects of water, phosphate buffer and borate buffer solution on catalytic synthesis of alanyl-glutamine dipeptide by yeast whole cells were studied. 2.792 g of L-alanine methyl ester hydrochloride (200 mM L-Ala-OMe) and 5.848 g of L-glutamine (400 mM L-Gln) were weighed and dissolved in 90 mL of the above three different reaction solutions respectively, and the recombinant S. cerevisiae was added to the reaction system to make $OD_{620}$=0.5-5.0 in the reaction solution, and the pH was kept at 8.5 with 6M NaOH solution at a controlled temperature of 25° C. for catalytic synthesis reaction. Samples were taken at a fixed point at 10/30/60 min, centrifuged to terminate the enzyme reaction, then the supernatant was taken and stored at 4° C. respectively. The concentration of alanyl-glutamine dipeptide was determined by high performance liquid chromatography (Appendix V D, part II, Chinese Pharmacopoeia, 2010 edition), and it was found that the most suitable reaction solution was phosphate buffer solution.

Example 20

Figure 7:
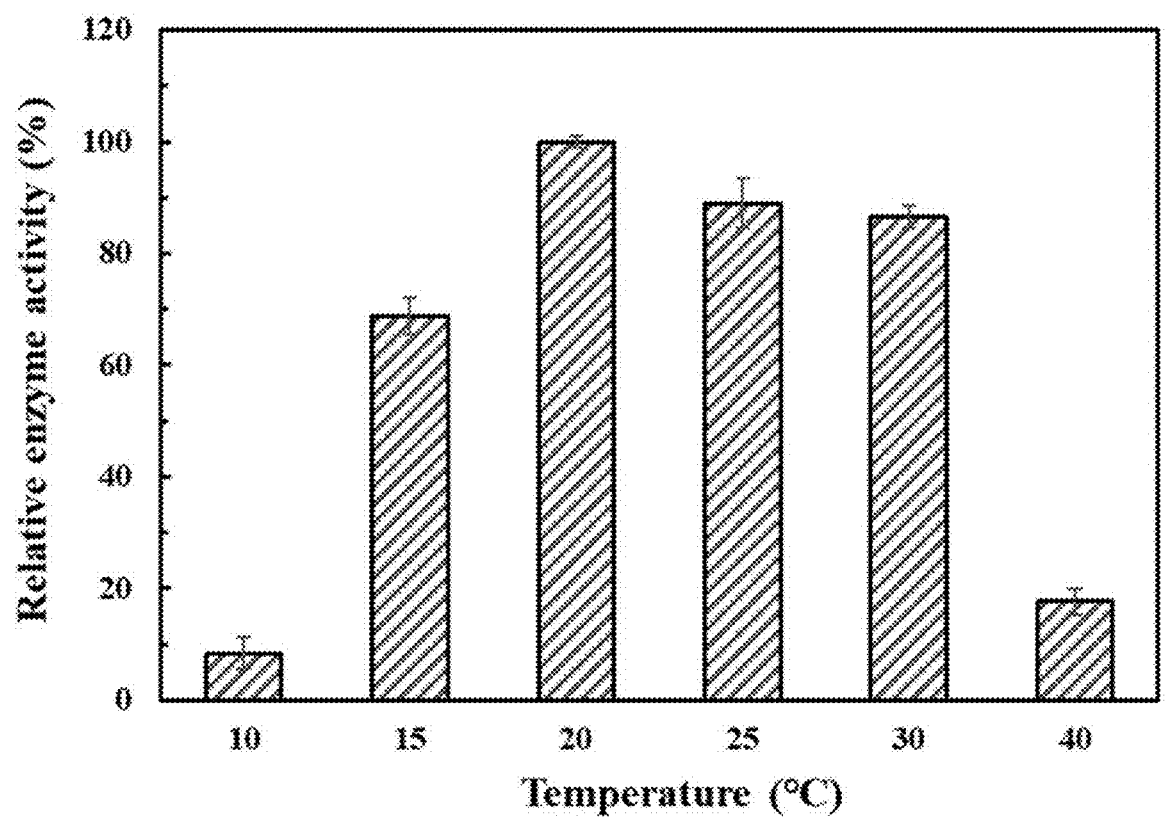
FIG. 7 is a graph showing the relative enzymatic activity of alanyl-glutamine dipeptide catalyzed by recombinant *S. cerevisiae* with the reaction temperature.

Effects of different reaction temperatures on catalytic synthesis of alanyl-glutamine dipeptide by yeast whole cells: The recombinant S. cerevisiae was cultured in the same manner as that in Example 12, and cells were collected by centrifugation for alanyl-glutamine dipeptide catalytic reaction. The effects of different reaction temperatures (10/15/20/25/30/40° C.) on the catalytic synthesis of alanyl-glutamine dipeptide by yeast whole cells were studied. 1.396 g of L-alanine methyl ester hydrochloride (100 mM L-Ala-OMe) and 2.924 g of L-glutamine (200 mM L-Gln) were weighed and dissolved in 90 mL of 0.2 M pH 8.7 phosphate buffer solution. The recombinant S. cerevisiae was added to the reaction system to make $OD_{620}$=0.5-5.0 in the reaction solution, and the pH was kept at 8.5 with 6 M NaOH solution for catalytic synthesis reaction at the above different reaction temperatures. 30 min later, the solution was centrifuged to terminate the enzyme reaction, and the concentration of alanyl-glutamine dipeptide was determined by high performance liquid chromatography (Appendix V D, part II, Chinese Pharmacopoeia, 2010 edition). The results showed that the enzyme had a higher activity in a wide temperature range, and the optimal temperature for reaction was 20° C., but with small difference from that of 25° C. and 30° C. Considering the economic factors such as production energy consumption, enzymatic reaction can be carried out directly at room temperature (20-30° C.), as shown in FIG. 7.

Example 21

Figure 8:
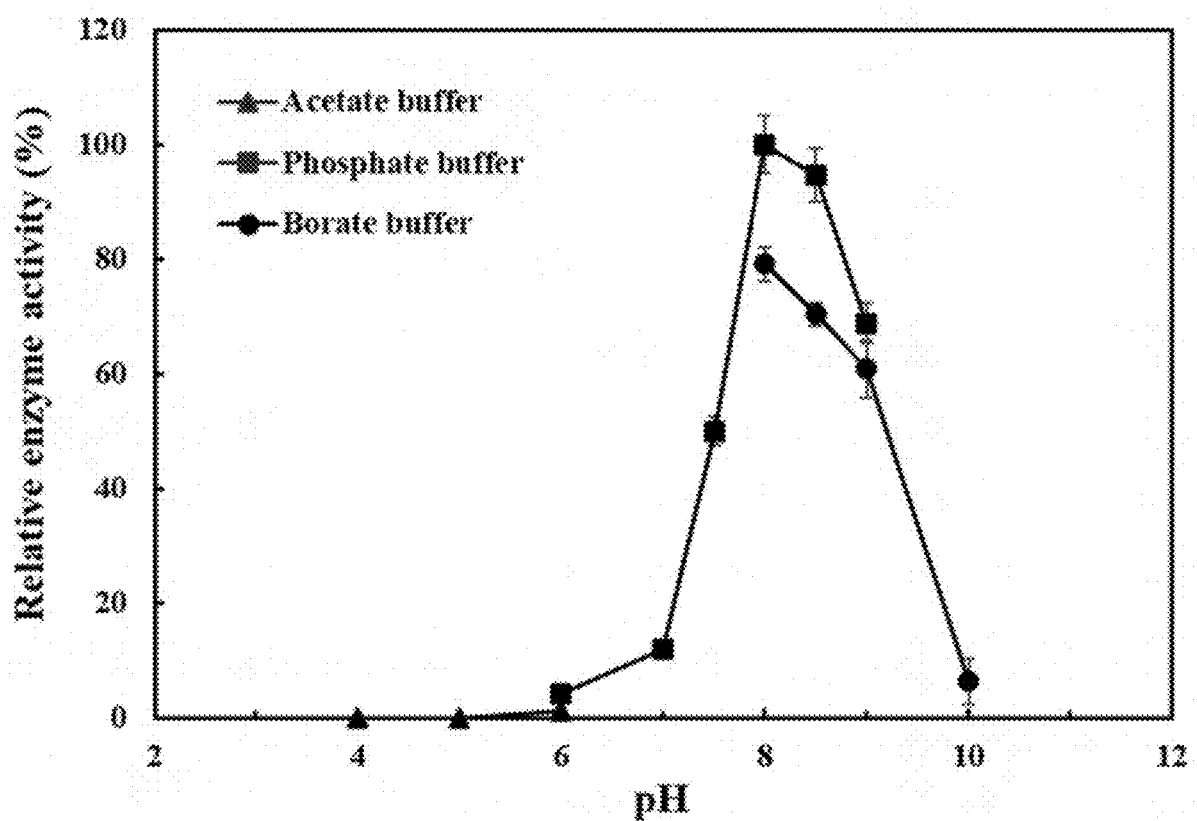
FIG. 8 is a graph showing the relative enzymatic activity of alanyl-glutamine dipeptide catalyzed by recombinant *S. cerevisiae* with the reaction pH value.

Effects of Different Reaction pH on Catalytic Synthesis of Alanyl-Glutamine Dipeptide by Yeast Whole Cells:

The recombinant S. cerevisiae was cultured in the same manner as that in Example 12, and cells were collected by centrifugation for alanyl-glutamine dipeptide catalytic reaction. The effects of different reaction pH (pH 4/5/6 (acetate buffer), 6/7/7.5/8/8.5/9 (phosphate buffer), 8/8.5/9/10 (borate buffer)) on the catalytic synthesis of alanyl-glutamine dipeptide by yeast whole cells were studied. 1.396 g of L-alanine methyl ester hydrochloride (100 mM L-Ala-OMe) and 2.924 g of L-glutamine (200 mM L-Gln) were weighed and dissolved in 90 mL of buffer solution, and recombinant S. Cerevisiae was added to the reaction system to make $OD_{620}$=0.5-5.0 in the reaction solution, and the temperature was controlled at 20° C., and the catalytic synthesis reaction was carried out under different reaction pH which was maintained by 6M NaOH solution. After reaction for 30 min, the solution was centrifuged to terminate enzymatic reaction. The concentration of alanyl-glutamine dipeptide was determined by high performance liquid chromatography (Appendix V D, part II, Chinese Pharmacopoeia, 2010 edition). The results showed that the enzyme had a higher activity in a wide pH range, and the optimal pH for reaction was 8.0, which verified that the optimal reaction solution of substrate was phosphate buffer solution, as shown in FIG. 8.

Example 22

Figure 9:
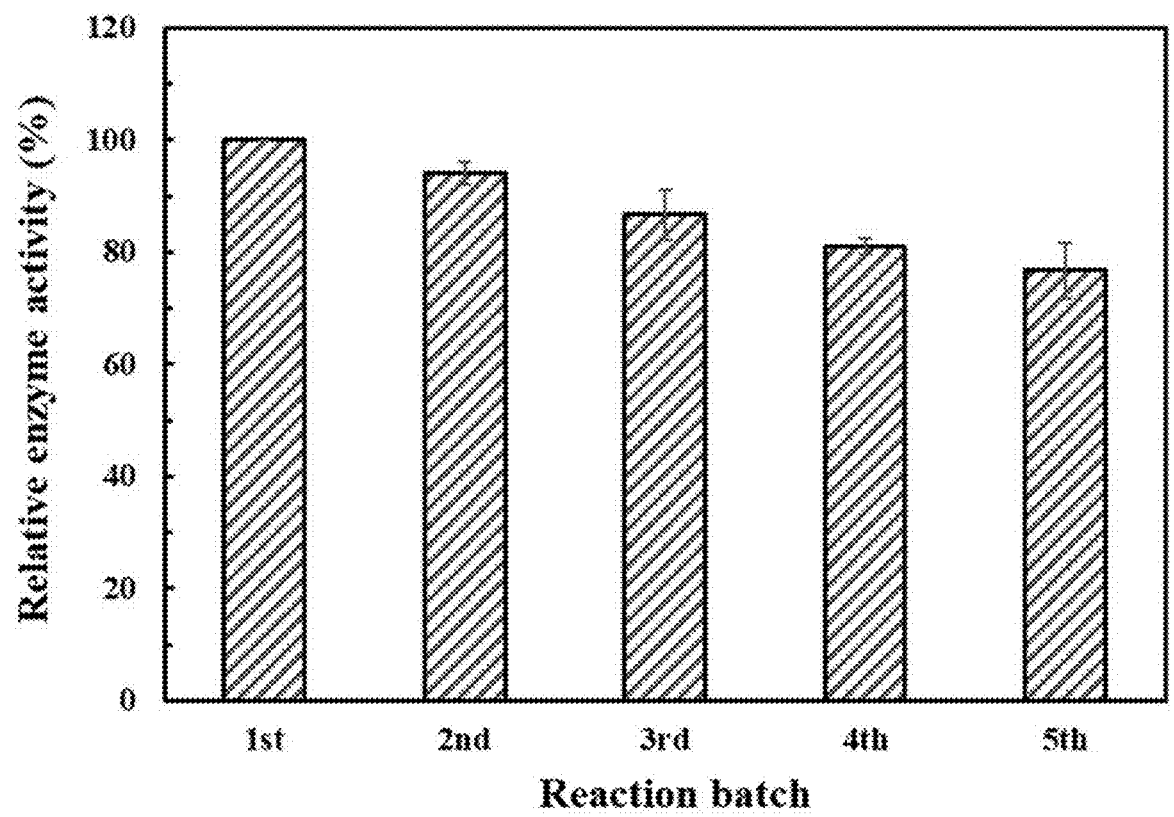
FIG. 9 is a graph showing the relative enzyme activity of recombinant *S. cerevisiae* with the number of times of recycling.

Efficient synthesis of alanyl-glutamine dipeptide by recycling of recombinant *S. cerevisiae*: The recombinant *S. cerevisiae* was cultured in the same manner as that in Example 12, and cells were collected by centrifugation for alanyl-glutamine dipeptide catalytic reaction. The reaction conditions were as follows: 0.698 g of L-alanine methyl ester hydrochloride (50 mM L-Ala-OMe) and 1.462 g of L-glutamine (100 mM L-Gln) were dissolved in 90 mL of buffer at a controlled temperature of 20° C. The pH of solution was adjusted to 8 with 6 M NaOH solution, samples were taken at fixed point at 20/30 min, centrifuged to terminate the enzyme reaction. Then, after the reaction supernatant was pumped out by a peristaltic pump or centrifuged, the reaction was repeated several times in accordance with the above reaction conditions. Finally, the concentration of alanyl-glutamine dipeptide was determined by high performance liquid chromatography (Appendix V D, part II, Chinese Pharmacopoeia, 2010 edition). The relative enzyme activity of the first reaction recombinant *S. cerevisiae* cells was defined as 100%, then the relative enzyme activity of the second reaction yeast cells was determined to be 94.0%; and the relative activity of the third reaction yeast cells was 86.7%; the relative enzyme activity of the fourth reaction yeast cells was 81.0%; the relative activity of the fifth reaction yeast cells was 76.7%, as shown in FIG. 9. During the process of recovering bacterial cells, partial cells were lost, therefore, the enzymatic activity in the process of catalyzed synthesis of alanyl-glutamine dipeptide by recombinant *S. cerevisiae* for repeated cycles was stable, and can be reused, to reduce the industrial production cost and solve the problems of difficulty in enzyme recovery and low utilization rate, etc., and meet the requirements of industrial production.

Example 23

Constructions of Self-Flocculating Recombinant *S. cerevisiae*:

Based on the recombinant *S. cerevisiae* constructed as in Example 11, in order to achieve its vector-free self-immobilization in the reactor, the upstream and downstream primer SEQ ID NO: 6/7 were designed according to the NCBI published flocculation gene FLO1 nucleotide sequence. The *Saccharomyce S. Cerevisiae* S288c genome was used as a template to amplify the flocculating gene (SEQ ID NO: 8).

Among them, PCR reaction system: dNTPs (2.5 mM each), 4 µL; 10*Buffer, 5 µL; F (10 µM), 2 µL; R (10 µM), 2 µL; template, 2 µL; Taq enzyme (5 U/µL), 1 µL; ddH$_2$O, 34 µL.

PCR reaction conditions: 94° C., 5 min, 1 cycle; 94° C., 30 sec, 55° C., 30 sec, 72° C., 5 min, 30 cycles; 72° C., 10 min, 1 cycle. The product was stored at 4° C.

At the end of PCR reaction, 2 µL of PCR product was detected by agarose gel electrophoresis, and the amplified PCR product was purified by PCR product purification kit (OMEGA, USA) and stored in a refrigerator at −20° C. for standby use.

Figure 10:
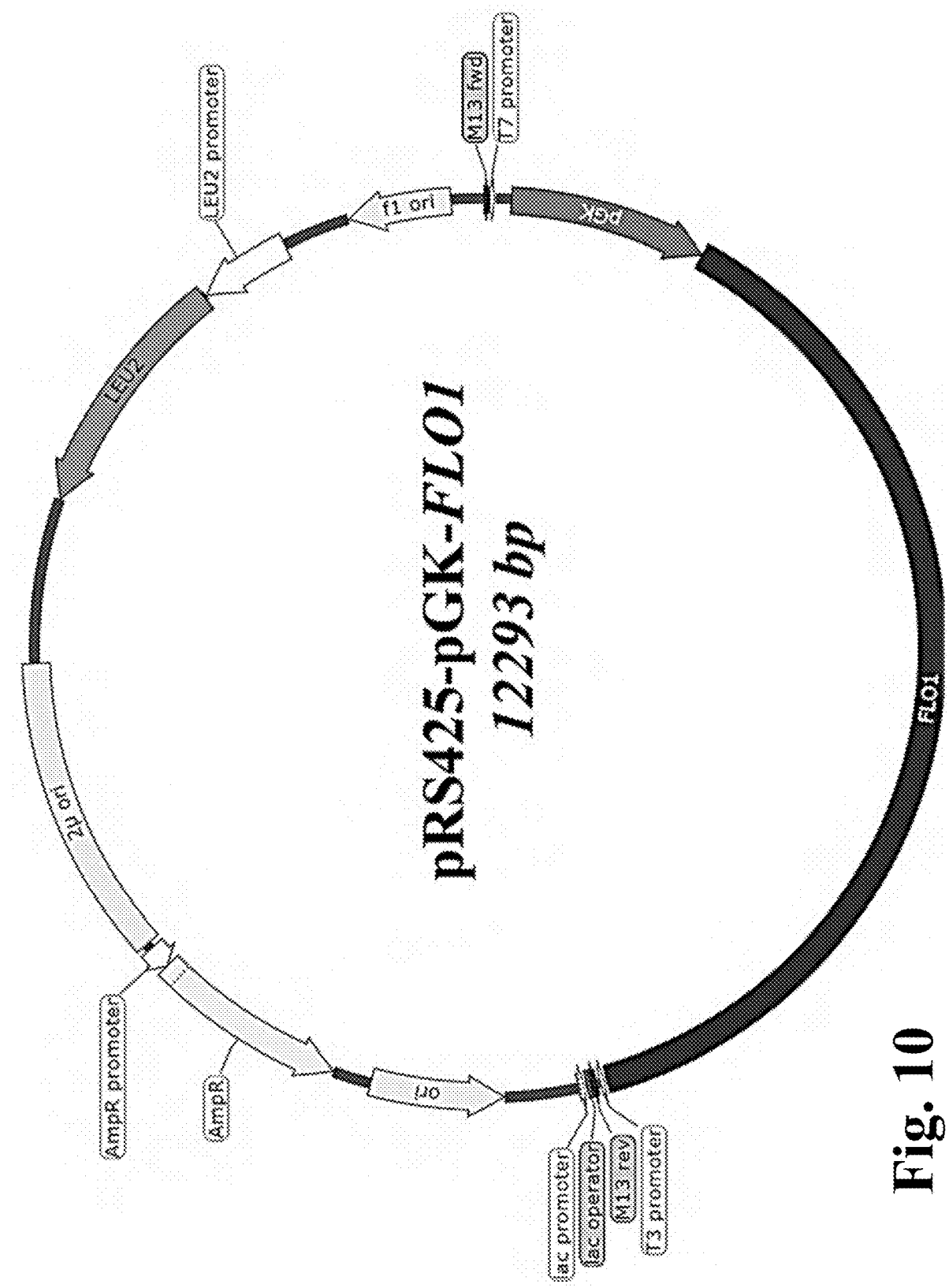
FIG. 10 is a schematic diagram showing the structure of a recombinant expression vector for self-flocculating recombinant *S. cerevisiae*.

The PCR product and the expression vector pRS425-pGK were digested and ligated overnight, and the ligated product was transformed into *E. coli* DH5a competent cells, and the transformants were screened on the LB-resistant medium plate and PCR and restriction enzyme digestion were carried out respectively, after verification, a self-flocculating recombinant vector was obtained, as shown in FIG. 10. In competent cells of recombinant *S. cerevisiae* constructed in Example 11 by chemical method, the self-flocculating recombinant *S. cerevisiae* of millimeter-sized flocculating particles was obtained by LEU-deficient type screening. The constructed self-flocculating recombinant *S. cerevisiae* had a fast flocculation rate and could be completely settled within 1-5 seconds, and the flocculated particles are moderately sized, with the size of 2-4 mm. The fermentation culture of self-flocculating recombinant *S. cerevisiae* was carried out as that in Example 12.

Example 24

Catalytic Synthesis of Alanyl-Glutamine Dipeptide by Self-Flocculating Recombinant *S. cerevisiae* and its Recycling:

The self-flocculating recombinant *S. cerevisiae* constructed in Example 23 was used to directly catalyze the synthesis of alanyl-glutamine dipeptide under the substrate concentration of (200 mM L-Ala-OMe, 100 mM L-Gln).

Figure 11:
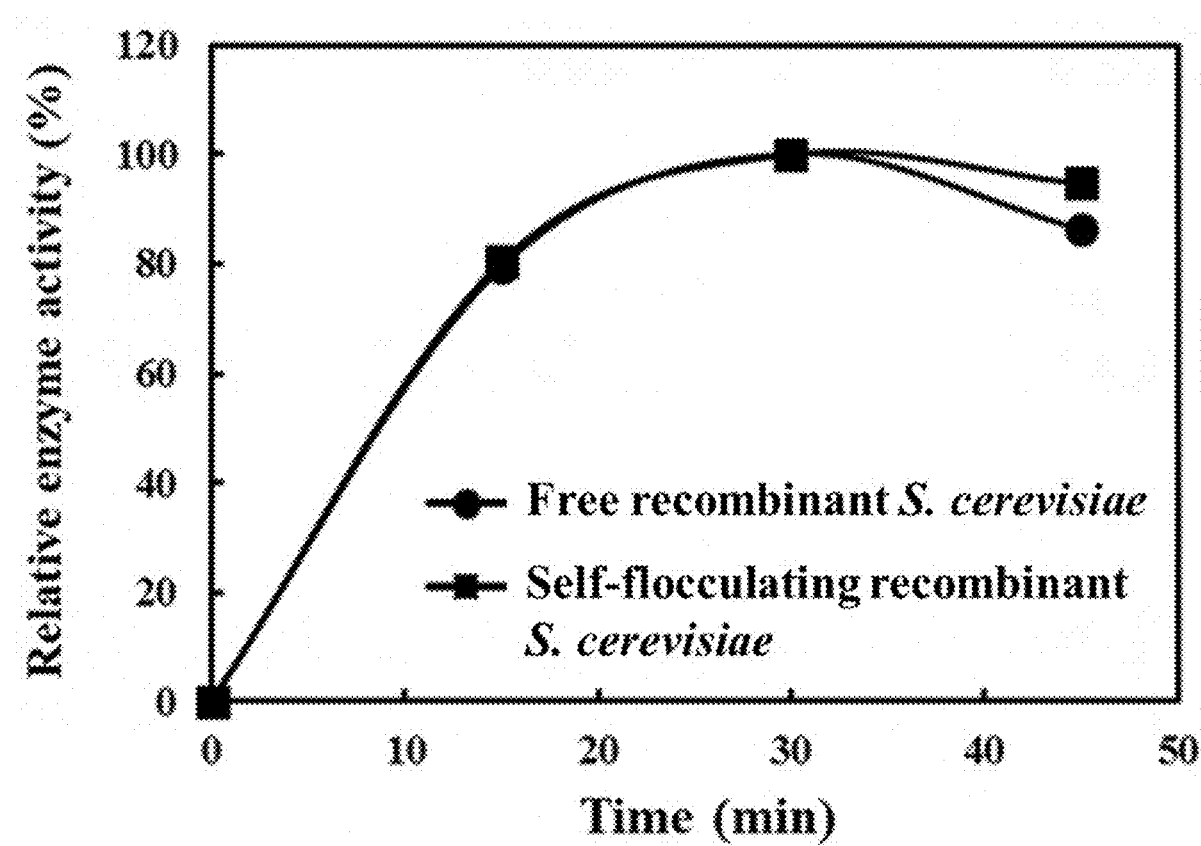
FIG. 11 is a graph showing the relative enzyme activity of self-flocculating recombinant *S. cerevisiae* with the time.

2.792 g of L-alanine methyl ester hydrochloride (200 mM L-Ala-OMe) and 1.462 g of L-glutamine (100 mM L-Gln) were weighed and dissolved in 90 mL of 0.2 M pH 8.7 phosphate buffer. The temperature was controlled at 20° C., and the pH was adjusted to 8.5 with a 6 M NaOH solution, and sample application was performed and stored at 4° C. The self-flocculating recombinant *S. cerevisiae* was added to the reaction system, and the pH was stabilized with 6 M NaOH solution, samples were taken at 15/30/45 min respectively, centrifuged to terminate the reaction and stored at 4° C. The concentration of alanyl-glutamine dipeptide in different reaction time was determined by high performance liquid chromatography (Appendix V D, part II, Chinese Pharmacopoeia, 2010 edition). The results were shown in FIG. 11. The self-flocculating recombinant *S. cerevisiae* constructed in Example 23 had the same catalytic activity of that of recombinant *S. cerevisiae* constructed in Example 11. The size of flocculated particles was appropriate, with little effect on mass transfer resistance and with a significant advantage for maintaining a high accumulation of alanyl-glutamine dipeptide.

Figure 12:
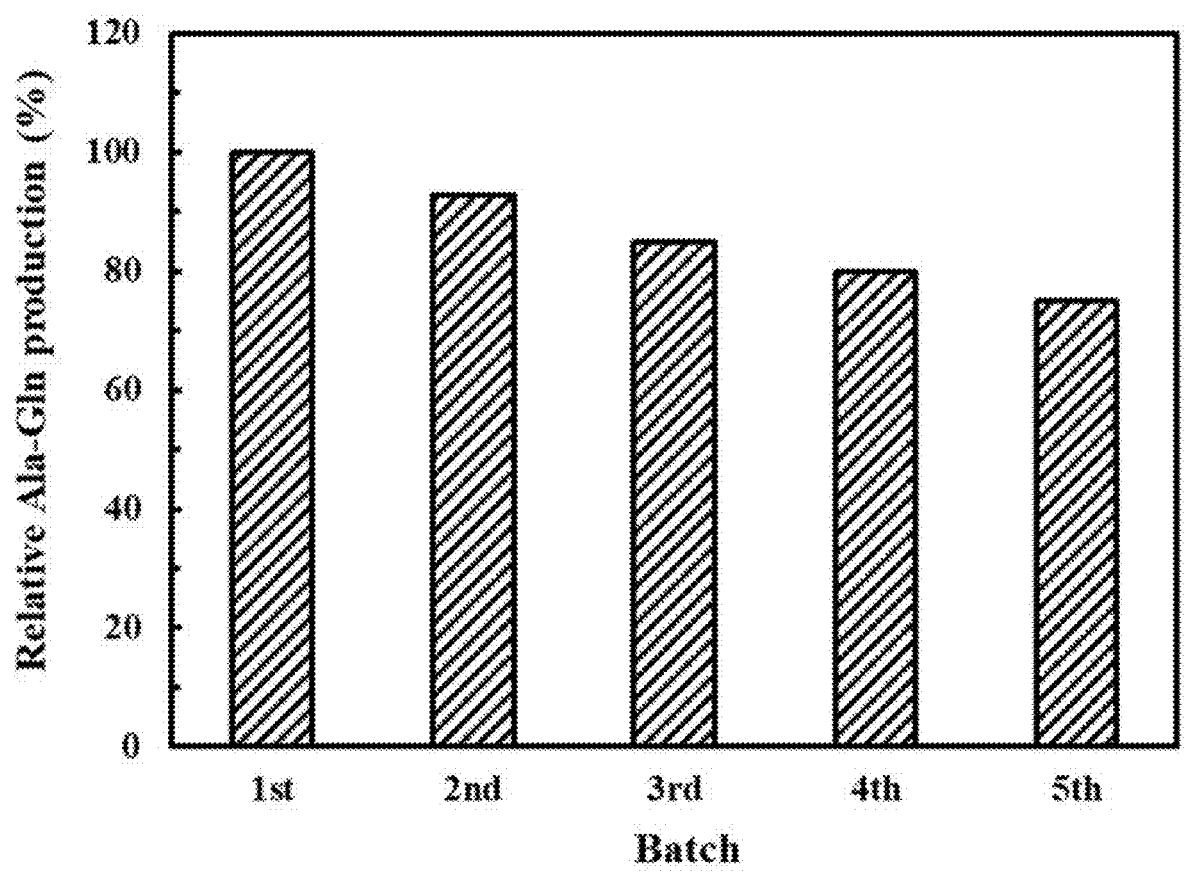
FIG. 12 is a graph showing the relative enzyme activity of self-flocculating recombinant *S. cerevisiae* with the number of times of recycling.

Further Investigation on the Effect of Sub-Self-Flocculating Recombinant *S. cerevisiae* Recycling on the Synthesis of Alanyl-Glutamine Dipeptide:

The recycling test method of self-flocculating recombinant *S. cerevisiae* was carried out in the same manner as in Example 22, and the concentration of alanyl-glutamine dipeptide was measured by high performance liquid chromatography (Appendix V D, part II, Chinese Pharmacopoeia, 2010 edition). The relative enzyme activity of the first reaction recombinant *S. cerevisiae* cells was defined as 100%, then the relative enzyme activity of the second reaction yeast cells was calculated as 92.6%, and the relative activity of the third reaction yeast cells was 84.8%; the relative enzyme activity of the fourth reaction yeast cells was 79.9%; the relative activity of the fifth reaction yeast cells was 75.1%, as shown in FIG. 12. The results showed that the repeated recycling of self-flocculating recombinant *SaccharomyceS. Cerevisiae* could maintain stable catalytic activity and good reproducibility, to achieve vector-free self-immobilization, coupling growth and catalysis in the reactor. It could omit the centrifugation and recovery steps of bacterial cells, reduce the production cost, therefore, it is more compliance with the green and economical industrial production mode.

What is claimed is:

1. A gene encoding alanyl-glutamine dipeptide synthetase, comprising the nucleotide sequence of SEQ ID NO: 1.

2. An alanyl-glutamine dipeptide synthetase, encoded by the gene of claim 1, comprising the amino acid sequence of SEQ ID NO: 2.

3. A recombinant *E. coli*. obtained by transfecting the gene of claim 1 into *Escherichia coli*.

4. A biosynthesis method of alanyl-glutamine dipeptide, comprising a step of transforming a substrate using the recombinant *E. coli*. of claim 3,
   wherein the substrate comprises a carboxyl component and an amine component, the carboxyl component is selected from the group consisting of amino acid esters and amino acid amides, the amine component is selected from the group consisting of amino acids, C-protected amino acids and amines.

5. The method according to claim 4, further comprising the following steps:
   (1) dissolving the substrate L-alanine methyl ester hydrochloride and L-glutamine in a buffer solution, and adjusting the pH to 8.0-10.0;
   (2) adding the recombinant *E. coli* to a system obtained in step (1) to react, with the reaction temperature of 15 to 40° C., and pH of the reaction system of 8.0 to 10.0;
   (3) collecting the reaction solution and centrifuging to separate bacterial cells and terminate the reaction at the reaction end point when pH is not lowered any longer.

6. The method according to claim 5, further comprising a step of recycling the bacterial cells of recombinant *E. coli*.

7. A recombinant *S. cerevisiae*, comprising a gene of claim 1.

8. The recombinant *S. cerevisiae* according to claim 7, further comprising an exogenous flocculating gene FLO1.

9. A biosynthesis method of alanyl-glutamine dipeptide, comprising the step of transforming a substrate using the recombinant *S. cerevisiae* of claim 7,
   wherein the substrate comprises a carboxyl component and an amine component, the carboxyl component is selected from the group consisting of amino acid esters and amino acid amides, the amine component is selected from the group consisting of amino acids, C-protected amino acids and amines.

10. The method according to claim 9, further comprising the following steps:
    (1) dissolving the substrate L-alanine methyl ester hydrochloride and L-glutamine in a solvent system, and adjusting the pH to 8.0-9.0;
    (2) adding the recombinant *S. cerevisiae* to a system obtained in step (1) to react, with the reaction temperature of 10 to 40° C., and pH of the reaction system of 8.0 to 9.0;
    (3) collecting the reaction solution and centrifuging to separate yeast cells and terminate the reaction at the reaction end point when pH is not lowered any longer.

11. The method according to claim 10, further comprising a step of recycling recombinant *S. cerevisiae*.

* * * * *

SEQUENCE LISTING

<160> NUMBER OF SEQ ID NOS: 8

<210> SEQ ID NO 1
<211> LENGTH: 1860
<212> TYPE: DNA
<213> ORGANISM: Sphingobacterium siyangensis

<400> SEQUENCE: 1

```
atgaaaaata caatttcgtg cctaacttta gcgcttttaa gcgcaagcca gttacatgct      60
caaacagctg ccgactcggc ttatgttaga gatcattatg aaaagaccga agtagcaatc     120
cccatgcgag atgggaagaa attatttact gcgatctaca gtccaaaaga caaatccaag     180
aaatatccag ttttactcaa tagaacaccc tacacggttt ctccttatgg gcagaacgaa     240
tacaaaaaaa gcttgggaaa ctttccccaa atgatgcgtg aaggttatat tttcgtttat     300
caggatgtcc gtggcaagtg gatgagcgaa ggtgattttg aagatattcg tccgaccacc     360
tacagcaaag ataaaaaagc aatcgatgaa agtacggata cctatgatgc gcttgaatgg     420
ttacagaaaa atctcaaaaa ctataatgac aaagccgggc tctatgggat ttcctatcca     480
ggcttctatt ctaccgtcgg attggtcaaa acacaccga gcttgaaggc agtctcccca     540
caggctcccg taacagactg gtttatcggc gacgacttcc accataatgg cgtattgttt     600
cttcaggatg catttacatt catgtcaacc tttggtgtcc cacgtccaaa acccattaca     660
ccggatcaat ttaagggcaa aattcaaatc aaagaagccg ataaatataa cttttttgca     720
gaagcaggaa cagcgcggga actcaaagaa aagtattttg gtgactccgt acaattttgg     780
aatggcctgt ttaaacatcc cgactatgat gattttttgga aatcgcgtgt gatcaccaat     840
tctttacagg aggtaaaacc agctgtgatg gtggttggtg gtttctttga cgcggaagat     900
gcttatggaa catttaagac ttaccaatcg attgaggata aaagcaaaaa aaacaactcg     960
attttagtcg cgggaccttg gtatcatggc ggctgggttc gtgcagaagg aaactattta    1020
ggtgatatcc aatttgagaa aaaaaccagt attacttatc aggagcaatt tgaacaaccg    1080
tttttcaaat attacctaaa agatgaagga aacttcgccc cttccgaagc taacattttt    1140
gtctcaggca gcaacgaatg gaaacatttc gaacaatggc cgccaaaaaa tgtagagaca    1200
aaaaaactat acttccaacc tcaggggaaa cttggatttg acaaagttca acgtacagat    1260
tcctgggatg aatatgtaac agaccctaat aaacttgttc cgcatcaagg tgggttaatt    1320
caaaaccgaa cacgggagta tatggtagat gatcagcgtt tcgcagctag tcgccctgat    1380
gtcatggttt atcaaacgga accgttgacg gaggatctga cgatagtagg cccaatcaaa    1440
aacttcctca aagtctcctc aacaggaaca gacgcggact atgttgtcaa actgattgat    1500
gtatacccga acgatgctgc aagttatcaa ggaaaaacaa tggctggata tcaaatgatg    1560
gtacgtggtg agatcatggc ggggaaatac cgaaatggtt ttgataaagc acaggccttg    1620
```

```
actccaggta tggtcgaaaa ggttaatttt gaaatgccag acgttgcgca taccttcaaa    1680
aaaggacatc gcattatggt tcaggtacaa aactcatggt ttccgttagc agaacgaaat    1740
ccacaggtat tcttaccgtc ttatacagcc accaaagctg acttccgtaa ggctacccaa    1800 cgtattttc acgatgtgaa caatgccaca tacatcgaat tttctgtcct caaagattag    1860
```

<210> SEQ ID NO 2
<211> LENGTH: 619
<212> TYPE: PRT
<213> ORGANISM: Sphingobacterium siyangensis

<400> SEQUENCE: 2

```
Met Lys Asn Thr Ile Ser Cys Leu Thr Leu Ala Leu Leu Ser Ala Ser
1               5                   10                  15

Gln Leu His Ala Gln Thr Ala Ala Asp Ser Ala Tyr Val Arg Asp His
            20                  25                  30

Tyr Glu Lys Thr Glu Val Ala Ile Pro Met Arg Asp Gly Lys Lys Leu
        35                  40                  45

Phe Thr Ala Ile Tyr Ser Pro Lys Asp Lys Ser Lys Lys Tyr Pro Val
    50                  55                  60

Leu Leu Asn Arg Thr Pro Tyr Thr Val Ser Pro Tyr Gly Gln Asn Glu
65                  70                  75                  80

Tyr Lys Lys Ser Leu Gly Asn Phe Pro Gln Met Met Arg Glu Gly Tyr
                85                  90                  95

Ile Phe Val Tyr Gln Asp Val Arg Gly Lys Trp Met Ser Glu Gly Asp
            100                 105                 110

Phe Glu Asp Ile Arg Pro Thr Thr Tyr Ser Lys Asp Lys Lys Ala Ile
        115                 120                 125

Asp Glu Ser Thr Asp Thr Tyr Asp Ala Leu Glu Trp Leu Gln Lys Asn
    130                 135                 140

Leu Lys Asn Tyr Asn Gly Lys Ala Gly Leu Tyr Gly Ile Ser Tyr Pro
145                 150                 155                 160

Gly Phe Tyr Ser Thr Val Gly Leu Val Lys Thr His Pro Ser Leu Lys
                165                 170                 175

Ala Val Ser Pro Gln Ala Pro Val Thr Asp Trp Phe Ile Gly Asp Asp
            180                 185                 190

Phe His His Asn Gly Val Leu Phe Leu Gln Asp Ala Phe Thr Phe Met
        195                 200                 205

Ser Thr Phe Gly Val Pro Arg Pro Lys Pro Ile Thr Pro Asp Gln Phe
    210                 215                 220

Lys Gly Lys Ile Gln Ile Lys Glu Ala Asp Lys Tyr Asn Phe Phe Ala
225                 230                 235                 240

Glu Ala Gly Thr Ala Arg Glu Leu Lys Glu Lys Tyr Phe Gly Asp Ser
                245                 250                 255

Val Gln Phe Trp Asn Asp Leu Pro Lys His Pro Asp Tyr Asp Asp Phe
            260                 265                 270

Trp Lys Ser Arg Val Ile Thr Asn Ser Leu Gln Glu Val Lys Pro Ala
        275                 280                 285

Val Met Val Val Gly Gly Phe Phe Asp Ala Glu Asp Ala Tyr Gly Thr
    290                 295                 300

Phe Lys Thr Tyr Gln Ser Ile Glu Asp Lys Ser Lys Lys Asn Asn Ser
305                 310                 315                 320

Ile Leu Val Ala Gly Pro Trp Tyr His Gly Gly Trp Val Arg Ala Glu
                325                 330                 335
```

```
Gly Asn Tyr Leu Gly Asp Ile Gln Phe Glu Lys Lys Thr Ser Ile Thr
                340                 345                 350

Tyr Gln Glu Gln Phe Glu Gln Pro Phe Lys Tyr Tyr Leu Lys Asp
            355                 360                 365

Glu Gly Asn Phe Ala Pro Ser Glu Ala Asn Ile Phe Val Ser Gly Ser
370                 375                 380

Asn Glu Trp Lys His Phe Glu Gln Trp Pro Lys Asn Val Glu Thr
385                 390                 395                 400

Lys Lys Leu Tyr Phe Gln Pro Gln Gly Lys Leu Gly Phe Asp Lys Val
                405                 410                 415

Gln Arg Thr Asp Ser Trp Asp Glu Tyr Val Thr Asp Pro Asn Lys Pro
                420                 425                 430

Val Pro His Gln Gly Gly Leu Ile Gln Asn Arg Thr Arg Glu Tyr Met
                435                 440                 445

Val Asp Asp Gln Arg Phe Ala Ala Ser Arg Pro Asp Val Met Val Tyr
450                 455                 460

Gln Thr Glu Pro Leu Thr Glu Asp Leu Thr Ile Val Gly Pro Ile Lys
465                 470                 475                 480

Asn Phe Leu Lys Val Ser Ser Thr Gly Thr Asp Ala Asp Tyr Val Val
                485                 490                 495

Lys Leu Ile Asp Val Tyr Pro Asn Asp Ala Ala Ser Tyr Gln Gly Lys
                500                 505                 510

Thr Met Ala Gly Tyr Gln Met Met Val Arg Gly Glu Ile Met Ala Gly
                515                 520                 525

Lys Tyr Arg Asn Gly Phe Asp Lys Ala Gln Ala Leu Thr Pro Gly Met
                530                 535                 540

Val Glu Lys Val Asn Phe Glu Met Pro Asp Val Ala His Thr Phe Lys
545                 550                 555                 560

Lys Gly His Arg Ile Met Val Gln Val Gln Asn Ser Trp Phe Pro Leu
                565                 570                 575

Ala Glu Arg Asn Pro Gln Val Phe Leu Pro Ser Tyr Thr Ala Thr Lys
                580                 585                 590

Ala Asp Phe Arg Lys Ala Thr Gln Arg Ile Phe His Asp Val Asn Asn
                595                 600                 605

Ala Thr Tyr Ile Glu Phe Ser Val Leu Lys Asp
610                 615

<210> SEQ ID NO 3
<211> LENGTH: 31
<212> TYPE: DNA
<213> ORGANISM: Artificial sequence
<220> FEATURE:
<223> OTHER INFORMATION: synthesized

<400> SEQUENCE: 3
cgcggatcca tgaaaaatac aatttcgtgc c                                31

<210> SEQ ID NO 4
<211> LENGTH: 31
<212> TYPE: DNA
<213> ORGANISM: Artificial sequence
<220> FEATURE:
<223> OTHER INFORMATION: synthesized

<400> SEQUENCE: 4
ccgctcgagc taatctttga ggacagaaaa t                                31
```

<210> SEQ ID NO 5
<211> LENGTH: 1860
<212> TYPE: DNA
<213> ORGANISM: Sphingobacterium sp.

<400> SEQUENCE: 5

| | | | | | | |
|---|---|---|---|---|---|---|
| atgaaaaata | caatttcgtg | cctaacttta | gcgcttttaa | gcgcaagcca | gttacatgct | 60 |
| caaacagctg | ccgactcggc | ttatgttaga | gatcattatg | aaaagaccga | agtagcaatt | 120 |
| cccatgcgag | atgggaaaaa | attatttact | gcgatctaca | gtccaaaaga | caaatccaag | 180 |
| aaatatccag | ttttgctcaa | tagaacgccc | tacacggttt | ctccttatgg | gcagaacgaa | 240 |
| tacaaaaaaa | gtttgggaaa | cttteccaa | atgatgcgtg | aaggctatat | tttcgtttac | 300 |
| caggatgtcc | gtggcaagtg | gatgagcgaa | ggtgattttg | aagatatacg | tccgaccacg | 360 |
| tacagcaaag | ataaaaaagc | aatcgatgaa | agtacggata | cctatgatgc | gcttgaatgg | 420 |
| ttacagaaaa | atctcaaaaa | ctataatggc | aaagccgggc | tctatgggat | ttcctatcca | 480 |
| ggcttctatt | ctaccgtcgg | attggtcaaa | acacacccga | gcttgaaggc | agtctcccca | 540 |
| caggctcccg | taacagactg | gtatatcggc | gacgacttcc | accataatgg | cgtattgttt | 600 |
| cttcaggatg | catttacatt | catgtcaacc | tttggtgtcc | ctcgtccaaa | acccattaca | 660 |
| ccggatcaat | ttaagggcaa | aattcagatc | aaagaagccg | ataaatataa | cttttttgca | 720 |
| gaagcaggaa | cagcgcggga | actcaaagaa | aaatactttg | gtgactccgt | acaattttgg | 780 |
| aatgacctgt | ttaagcatcc | cgactatgat | gattttggα | aatcgcgtgt | gatcaccaat | 840 |
| tcttttacagg | aggtaaaacc | agctgtgatg | gtggttggtg | gtttctttga | cgcggaagat | 900 |
| gcttatggaa | catttaagac | ctaccaatcg | attgaggata | aaagcaaaaa | aaacaactcg | 960 |
| attttagtcg | cgggaccttg | gtatcatggc | ggctgggttc | gtgcagaagg | aaactattta | 1020 |
| ggtgatatcc | aatttgagaa | aaaaccagt | attacttatc | aggaacaatt | tgaacaaccg | 1080 |
| ttttttcaaat | attacctaaa | agatgaagga | aacttcgccc | cttccgaagc | caacattttt | 1140 |
| gtttcaggca | gcaacgaatg | gaaacatttc | gaacaatggc | caccaaaaaa | tgtagagaca | 1200 |
| aaaaaactat | acttccaacc | tcaggggaaa | cttggatttg | acaaagttca | acgtacagat | 1260 |
| tcctgggatg | aatatgtaac | agacccgaat | aaacctgttc | cgcatcaagg | tgggttaatt | 1320 |
| caaaaccgaa | cacgggagta | tatggtagat | gatcaacgtt | tcgcggctag | tcgccctgat | 1380 |
| gtcatggttt | atcaaacgga | accgttgacg | gaggacctga | cgatagtagg | cccaatcaaa | 1440 |
| aactttctca | agtttcttc | aacaggaaca | gacgcggact | atgttgtcaa | actgattgac | 1500 |
| gtttatccga | atgatgcagc | aagttatcaa | ggaaaaacaa | tggctggata | tcaaatgatg | 1560 |
| gtacgtggtg | agatcatggc | ggggaaatac | cgaaatggtt | tcgataaagc | gcaggccttg | 1620 |
| actccaggta | tggtcgaaaa | ggtgaatttt | gaaatgccag | acgttgcgca | taccttcaaa | 1680 |
| aaaggacatc | gcattatggt | tcaggtacaa | aactcatggt | ttccgctggc | agaacgaaat | 1740 |
| ccacaggtgt | ttttagcacc | ttatacagct | accaaagctg | atttccgcaa | agctacccaa | 1800 |
| cgtatttttc | acgatgtgaa | caatgccaca | tacatcgaat | tttctgtcct | caaagattag | 1860 |

<210> SEQ ID NO 6
<211> LENGTH: 36
<212> TYPE: DNA
<213> ORGANISM: Artificial sequence
<220> FEATURE:
<223> OTHER INFORMATION: synthesized

<400> SEQUENCE: 6

```
cagcgcggat ccatgacaat gcctcatcgc tatatg                                36
```

<210> SEQ ID NO 7
<211> LENGTH: 38
<212> TYPE: DNA
<213> ORGANISM: Artificial sequence
<220> FEATURE:
<223> OTHER INFORMATION: synthesized

<400> SEQUENCE: 7

```
ataagaatgc ggccgcttaa ataattgcca gcaataag                              38
```

<210> SEQ ID NO 8
<211> LENGTH: 4614
<212> TYPE: DNA
<213> ORGANISM: Saccharomyces cerevisiae

<400> SEQUENCE: 8

```
atgacaatgc ctcatcgcta tatgttttg gcagtcttta cacttctggc actaactagt       60
gtggcctcag gagccacaga ggcgtgctta ccagcaggcc agaggaaaag tgggatgaat      120
ataaatttt accagtattc attgaaagat tcctccacat attcgaatgc agcatatatg      180
gcttatggat atgcctcaaa aaccaaacta ggttctgtcg gaggacaaac tgatatctcg     240
attgattata atattcctg tgttagttca tcaggcacat ttccttgtcc tcaagaagat      300
tcctatggaa actgggatg caaaggaatg ggtgcttgtt ctaatagtca aggaattgca      360
tactggagta ctgatttatt tggtttctat actaccccaa caaacgtaac cctagaaatg      420
acaggttatt ttttaccacc acagacgggt tcttacacat tcaagtttgc tacagttgac      480
gactctgcaa ttctatcagt aggtggtgca accgcgttca actgttgtgc tcaacagcaa      540
ccgccgatca catcaacgaa ctttaccatt gacggtatca agccatgggg tggaagtttg      600
ccacctaata tcgaaggaac cgtctatatg tacgctggct actattatcc aatgaaggtt      660
gtttactcga acgctgtttc ttggggtaca cttccaatta gtgtgacact tccagatggt      720
accactgtaa gtgatgactt cgaagggtac gtctattcct ttgacgatga cctaagtcaa      780
tctaactgta ctgtccctga cccttcaaat tatgctgtca gtaccactac aactacaacg      840
gaaccatgga ccggtacttt cacttctaca tctactgaaa tgaccaccgt caccggtacc      900
aacggcgttc caactgacga aaccgtcatt gtcatcagaa ctccaacaac tgctagcacc      960
atcataacta caactgagcc atggaacagc acttttacct ctacttctac cgaattgacc     1020
acagtcactg gcaccaatgg tgtacgaact gacgaaacca tcattgtaat cagaacacca     1080
acaacagcca ctactgccat aactacaact gagccatgga acagcacttt tacctctact     1140
tctaccgaat tgaccacagt caccggtacc aatggtttgc aactgatga accatcatt     1200
gtcatcagaa caccaacaac agccactact gccatgacta caactcagcc atggaacgac     1260
acttttacct ctacttctac cgaattgacc acagtcaccg gtaccaatgg tttgccaact     1320
gatgagacca tcattgtcat cagaacacca acaacagcca ctactgccat gactacaact     1380
cagccatgga cgacactttt acctctact tctaccgaat tgaccacagt caccggtacc     1440
aatggtttgc caactgatga accatcatt gtcatcagaa caccaacaac agccactact     1500
gccatgacta caactcagcc atggaacgac acttttacct ctacatccac tgaaatcacc     1560
accgtcaccg gtaccaatgg tttgccaact gatgagacca tcattgtcat cagaacacca     1620
acaacagcca ctactgccat gactacacct cagccatgga cgacactttt acctctaca     1680
```

```
tccactgaaa tgaccaccgt caccggtacc aacggtttgc caactgatga aaccatcatt    1740
gtcatcagaa caccaacaac agccactact gccataacta caactgagcc atggaacagc    1800
acttttacct ctacatccac tgaaatgacc accgtcaccg gtaccaacgg tttgccaact    1860
gatgaaacca tcattgtcat cagaacacca acaacagcca ctactgccat aactacaact    1920
cagccatgga acgacacttt tacctctaca tccactgaaa tgaccaccgt caccggtacc    1980
aacggtttgc caactgatga aaccatcatt gtcatcagaa caccaacaac agccactact    2040
gccatgacta caactcagcc atggaacgac acttttacct ctacatccac tgaaatcacc    2100
accgtcaccg gtaccaccgg tttgccaact gatgagacca tcattgtcat cagaacacca    2160
acaacagcca ctactgccat gactacaact cagccatgga acgacacttt tacctctaca    2220
tccactgaaa tgaccaccgt caccggtacc aacggcgttc caactgacga aaccgtcatt    2280
gtcatcagaa ctccaactag tgaaggtcta atcagcacca ccactgaacc atggactggt    2340
actttcacct ctacatccac tgagatgacc accgtcaccg gtactaacgg tcaaccaact    2400
gacgaaaccg tgattgttat cagaactcca accagtgaag gtttggttac aaccaccact    2460
gaaccatgga ctggtacttt tacttctaca tctactgaaa tgaccaccat tactggaacc    2520
aacggcgttc caactgacga aaccgtcatt gtcatcagaa ctccaaccag tgaaggtcta    2580
atcagcacca ccactgaacc atggactggt acttttactt ctacatctac tgaaatgacc    2640
accattactg gaaccaatgg tcaaccaact gacgaaaccg ttattgttat cagaactcca    2700
actagtgaag gtctaatcag cactacaacg gaaccatgga ccggtacttt cacttctaca    2760
tctactgaaa tgacgcacgt caccggtacc aacggcgttc caactgacga aaccgtcatt    2820
gtcatcagaa ctccaaccag tgaaggtcta atcagcacca ccactgaacc atggactggc    2880
actttcactt cgacttccac tgaggttacc accatcactg gaaccaacgg tcaaccaact    2940
gacgaaactg tgattgttat cagaactcca accagtgaag gtctaatcag caccaccact    3000
gaaccatgga ctggtacttt cacttctaca tctactgaaa tgaccaccgt caccggtact    3060
aacggtcaac caactgacga aaccgtgatt gttatcagaa ctccaaccag tgaaggtttg    3120
gttacaacca ccactgaacc atggactggt acttttactt cgacttccac tgaaatgtct    3180
actgtcactg gaaccaatgg cttgccaact gatgaaactg tcattgttgt caaaactcca    3240
actactgcca tctcatccag tttgtcatca tcatcttcag gacaaatcac cagctctatc    3300
acgtcttcgc gtccaattat taccccattc tatcctagca atggaacttc tgtgatttct    3360
tcctcagtaa tttcttcctc agtcacttct tctctattca cttcttctcc agtcatttct    3420
tcctcagtca tttcttcttc tacaacaacc tccacttcta tattttctga atcatctaaa    3480
tcatccgtca ttccaaccag tagttccacc tctggttctt ctgagagcga aacgagttca    3540
gctggttctg tctcttcttc ctcttttatc tcttctgaat catcaaaatc tcctacatat    3600
tcttcttcat cattaccact tgttaccagt gcgacaacaa gccaggaaac tgcttcttca    3660
ttaccacctg ctaccactac aaaaacgagc gaacaaacca ctttggttac cgtgacatcc    3720
tgcgagtctc atgtgtgcac tgaatccatc tcccctgcga ttgtttccac agctactgtt    3780
actgttagcg gcgtcacaac agagtatacc acatggtgcc ctatttctac tacagagaca    3840
acaaagcaaa ccaaagggac aacagagcaa accacagaaa caacaaaaca aaccacggta    3900
gttacaattt cttcttgtga atctgacgta tgctctaaga ctgcttctcc agccattgta    3960
tctacaagca ctgctactat taacggcgtt actacagaat acacaacatg gtgtcctatt    4020
tccaccacag aatcgaggca acaaacaacg ctagttactg ttacttcctg cgaatctggt    4080
```

```
gtgtgttccg aaactgcttc acctgccatt gtttcgacgg ccacggctac tgtgaatgat    4140
gttgttacgg tctatcctac atggaggcca cagactgcga atgaagagtc tgtcagctct    4200
aaaatgaaca gtgctaccgg tgagacaaca accaatactt tagctgctga aacgactacc    4260
aatactgtag ctgctgagac gattaccaat actggagctg ctgagacgaa aacagtagtc    4320
acctcttcgc tttcaagatc taatcacgct gaaacacaga cggcttccgc gaccgatgtg    4380
attggtcaca gcagtagtgt tgtttctgta tccgaaactg gcaacaccaa gagtctaaca    4440
agttccgggt tgagtactat gtcgcaacag cctcgtagca caccagcaag cagcatggta    4500
ggatatagta cagcttcttt agaaatttca acgtatgctg gcagtgccaa cagcttactg    4560
gccggtagtg gtttaagtgt cttcattgcg tccttattgc tggcaattat ttaa          4614
```